(12) United States Patent
Katrana et al.

(10) Patent No.: US 8,998,995 B2
(45) Date of Patent: Apr. 7, 2015

(54) ELBOW PROSTHESIS

(75) Inventors: Nicholas J. Katrana, Fort Wayne, IN (US); Nathan A. Winslow, Warsaw, IN (US); Thomas M. Vanasse, Warsaw, IN (US); Brian K. Berelsman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 9 days.

(21) Appl. No.: 13/465,690

(22) Filed: May 7, 2012

(65) Prior Publication Data

US 2012/0221113 A1 Aug. 30, 2012

Related U.S. Application Data

(63) Continuation-in-part of application No. 12/562,616, filed on Sep. 18, 2009, which is a continuation-in-part of application No. 12/391,904, filed on Feb. 24, 2009, which is a continuation-in-part of application No.

(Continued)

(51) Int. Cl.
*A61F 2/38* (2006.01)
*A61F 2/30* (2006.01)
*A61B 17/86* (2006.01)

(52) U.S. Cl.
CPC ........... *A61F 2/3804* (2013.01); *A61F 2/30767* (2013.01); *A61F 2002/30131* (2013.01);
(Continued)

(58) Field of Classification Search
CPC ................ A61F 2002/3813; A61F 2002/3818; A61F 2002/3831
USPC ............................................ 623/20.11–20.13
See application file for complete search history.

(56) References Cited

U.S. PATENT DOCUMENTS 3,547,115 A 12/1970 Stevens
3,694,821 A 10/1972 Moritz
(Continued)

FOREIGN PATENT DOCUMENTS

DE 2806717 8/1979
DE 3940728 A1 6/1991
(Continued)

OTHER PUBLICATIONS

DePuy Orthopaedics, Inc., web page print out—http://www/allaboutarthritis.com/AllAboutArthritis/layoutTemplates/html/en/contentdisplay/document/condition/arthritis/clinicalArticle/Elbow_Replacement_Surgery.htm, 2000-2005—printed Dec. 14, 2005.

(Continued)

*Primary Examiner* — Randy Shay
*Assistant Examiner* — Dinah Baria
(74) *Attorney, Agent, or Firm* — Harness, Dickey

(57) ABSTRACT

An elbow prosthesis according to the present teachings can include a stem structure and an articulating component. The stem structure can be operable to be positioned in a bone of a joint. The stem structure can include a stem portion that is operable to be positioned in the bone and a C-shaped body portion having a first retaining mechanism formed thereon. The articulating component can have a second retaining mechanism formed thereon. One of the first and second retaining mechanisms can include an extension portion and a first anti-rotation portion. The other retaining mechanism can include a receiving portion and a second anti-rotation portion. The articulating component can be advanced from an insertion position to an assembled position, such that the first and second mechanisms cooperatively interlock to inhibit translation and rotation of the articulating component relative to the C-shaped body portion of the stem structure.

3 Claims, 12 Drawing Sheets

Related U.S. Application Data

11/384,943, filed on Mar. 17, 2006, now Pat. No. 8,585,768, which is a continuation-in-part of application No. 10/333,140, filed as application No. PCT/US01/22338 on Jul. 17, 2001, now Pat. No. 7,247,170.

(60) Provisional application No. 60/219,103, filed on Jul. 18, 2000, provisional application No. 61/505,360, filed on Jul. 7, 2011.

(52) U.S. Cl.
CPC .......... A61F2002/30367 (2013.01); A61F 2002/30377 (2013.01); A61F 2002/30403 (2013.01); A61F 2002/30433 (2013.01); A61F 2002/30507 (2013.01); A61F 2002/30578 (2013.01); A61F 2002/30594 (2013.01); A61F 2002/30604 (2013.01); A61F 2002/30616 (2013.01); A61F 2002/3809 (2013.01); A61F 2002/3813 (2013.01); A61B 17/86 (2013.01); A61F 2002/30607 (2013.01)

(56) References Cited

U.S. PATENT DOCUMENTS

| | | | |
|---|---|---|---|
| 3,708,805 | A | 1/1973 | Scales et al. |
| 3,816,854 | A | 6/1974 | Schlein |
| 3,824,630 | A | 7/1974 | Johnston |
| 3,852,831 | A | 12/1974 | Dee et al. |
| 3,919,725 | A | 11/1975 | Swanson et al. |
| 3,939,496 | A | 2/1976 | Ling et al. |
| 3,946,445 | A | 3/1976 | Bentley et al. |
| 3,990,117 | A | 11/1976 | Pritchard et al. |
| 3,991,425 | A | 11/1976 | Martin et al. |
| 4,001,603 | A | 1/1977 | Wilcox |
| 4,008,495 | A | 2/1977 | Cavendish et al. |
| 4,011,603 | A | 3/1977 | Steffee |
| 4,038,704 | A | 8/1977 | Ring et al. |
| 4,079,469 | A | 3/1978 | Wadsworth et al. |
| 4,129,902 | A | 12/1978 | Harmon |
| 4,131,956 | A | 1/1979 | Treace |
| 4,131,957 | A | 1/1979 | Bokros |
| 4,194,250 | A | 3/1980 | Walker |
| 4,206,516 | A | 6/1980 | Pilliar |
| 4,224,695 | A | 9/1980 | Grundei et al. |
| 4,224,697 | A | 9/1980 | Murray et al. |
| 4,242,758 | A | 1/1981 | Amis et al. |
| 4,259,752 | A | 4/1981 | Taleisnik |
| 4,280,231 | A | 7/1981 | Swanson |
| 4,293,963 | A | 10/1981 | Gold et al. |
| 4,301,552 | A | 11/1981 | London |
| 4,352,212 | A | 10/1982 | Greene et al. |
| 4,378,607 | A | 4/1983 | Wadsworth et al. |
| 4,383,337 | A | 5/1983 | Volz et al. |
| 4,479,271 | A | 10/1984 | Bolesky et al. |
| 4,538,306 | A | 9/1985 | Dorre et al. |
| 4,659,331 | A | 4/1987 | Matthews et al. |
| 4,725,280 | A | 2/1988 | Laure |
| 4,759,768 | A | 7/1988 | Hermann et al. |
| 4,822,364 | A | 4/1989 | Inglis et al. |
| 4,911,719 | A | 3/1990 | Merle et al. |
| 4,927,422 | A | 5/1990 | Engelhardt |
| 4,936,853 | A | 6/1990 | Fabian et al. |
| 5,024,670 | A | 6/1991 | Smith et al. |
| 5,030,237 | A | 7/1991 | Sorbie et al. |
| 5,207,711 | A | 5/1993 | Caspari et al. |
| 5,282,367 | A | 2/1994 | Moore et al. |
| 5,282,867 | A | 2/1994 | Mikhail |
| 5,314,484 | A | 5/1994 | Huene |
| 5,376,121 | A | 12/1994 | Huene et al. |
| 5,380,334 | A | 1/1995 | Torrie et al. |
| 5,411,555 | A | 5/1995 | Nieder |
| 5,507,821 | A | 4/1996 | Sennwald et al. |
| 5,507,826 | A | 4/1996 | Besselink et al. |
| 5,549,685 | A | 8/1996 | Hayes |
| 5,584,835 | A | 12/1996 | Greenfield |
| 5,665,087 | A | 9/1997 | Huebner |
| 5,702,471 | A | 12/1997 | Grundei et al. |
| 5,725,541 | A | 3/1998 | Anspach, III et al. |
| 5,725,591 | A | 3/1998 | DeCarlo, Jr. et al. |
| 5,782,923 | A | 7/1998 | Engelbrecht et al. |
| 5,840,078 | A | 11/1998 | Yerys |
| 5,879,395 | A | 3/1999 | Tornier et al. |
| 5,980,557 | A | 11/1999 | Iserin et al. |
| 6,027,534 | A | 2/2000 | Wack et al. |
| 6,120,543 | A | 9/2000 | Kubein-Meesenburg et al. |
| 6,162,253 | A | 12/2000 | Conzemius et al. |
| 6,290,725 | B1 | 9/2001 | Weiss et al. |
| 6,306,171 | B1 | 10/2001 | Conzemius |
| 6,379,387 | B1 | 4/2002 | Tornier et al. |
| 6,626,906 | B1 | 9/2003 | Young |
| 6,656,225 | B2 | 12/2003 | Martin |
| 6,699,290 | B1 | 3/2004 | Wack et al. |
| 6,716,248 | B2 | 4/2004 | Huene |
| 6,767,368 | B2 | 7/2004 | Tornier et al. |
| 6,814,757 | B2 | 11/2004 | Kopylov et al. |
| 6,890,357 | B2 | 5/2005 | Tornier |
| 7,247,170 | B2 | 7/2007 | Graham et al. |
| 7,527,650 | B2 | 5/2009 | Johnson et al. |
| 2002/0165614 | A1 | 11/2002 | Tornier |
| 2004/0186580 | A1 | 9/2004 | Steinmann |
| 2004/0243243 | A1 | 12/2004 | Tornier |
| 2004/0254574 | A1 | 12/2004 | Morrison et al. |
| 2005/0216090 | A1 | 9/2005 | O'Driscoll et al. |
| 2006/0173546 | A1 | 8/2006 | Berelsman et al. |
| 2008/0015706 | A1 | 1/2008 | Berelsman et al. |
| 2008/0033566 | A1 | 2/2008 | Berelsman et al. |
| 2008/0154384 | A1 | 6/2008 | Acker et al. |
| 2008/0183291 | A1 | 7/2008 | Scheller et al. |
| 2008/0188942 | A1 | 8/2008 | Brown et al. |
| 2009/0105839 | A1 | 4/2009 | Ikegami et al. |
| 2010/0087928 | A1 | 4/2010 | Graham et al. |
| 2010/0305710 | A1* | 12/2010 | Metzger et al. ............ 623/20.31 |
| 2013/0345818 | A1 | 12/2013 | Wagner et al. |

FOREIGN PATENT DOCUMENTS

| | | |
|---|---|---|
| FR | 2419718 A1 | 10/1979 |
| FR | 2634373 | 1/1990 |
| GB | 1520162 | 8/1978 |
| SU | 1560183 A | 7/1988 |
| SU | 1567200 A | 5/1990 |

OTHER PUBLICATIONS

Discovery Elbow System brochure, Surgical Technique, Biomet Orthopedics, Inc., © 2002.

Joint Replacement, Overview, © DePuy Orthopaedics, Inc., www.jointreplacement.com/xq/ASP.default/mn.local/pg.list/joint_id.2/list_id.59/newFont.2/joint_nm.Elbow/local_id.18/qx/default.htm, 2000-2005.

Joint Replacement, Surgery, © DePuy Orthopaedics, Inc., www.jointreplacement.com/xq/ASP.default/mn.local/pg.list/joint_id.2/list_id.59/newFont.2/joint_nm.Elbow/local_id.18/qx/default.htm, 2000-2005.

International Search Report for PCT/US01/22338 mailed Jan. 3, 2002 based on U.S. Appl. No. 60/219,103, filed Jul. 18, 2000.

Latitude®, "Total Elbow Prosthesis, A new generation is born naturally precise", TORNIER [undated].

Latitude®, "Total Elbow Prosthesis, Surgical Technique", TORNIER pp. 1-39 [undated].

Sorbie-Questor® Total Elbow System, Extremities (2003) Wright Medical Technology, Inc., 1 page.

Non-Final Office Action for U.S. Appl. No. 11/384,943, mailed Apr. 13, 2010.

Final Office Action for U.S. Appl. No. 11/384,943, mailed Oct. 27, 2010.

Non-Final Office Action for U.S. Appl. No. 11/384,943, mailed Apr. 12, 2011.

International Search Report and Written Opinion for PCT/US2010/049314 mailed Feb. 21, 2011.

International Search Report and Written Opinion for PCT/US2009/057449 mailed Feb. 21, 2011.

(56) References Cited

OTHER PUBLICATIONS

International Prelliminary Report on Patentability and Written Opinion for PCT/US2009/057449 Mailed Sep. 9, 2011.
Final Office Action for U.S. Appl. No. 11/384,943 Mailed Dec. 12, 2011.
Non-Final Office Action for U.S. Appl. No. 12/391,904, mailed Nov. 1, 2012.
Non-Final Office Action regarding U.S. Appl. No. 12/780,424, mailed Nov. 2, 2012.
Non-Final Office Action regarding U.S. Appl. No. 12/562,616, mailed May 17, 2012.
International Search Report and Written Opinion of the International Searching Authority regarding International Application No. PCT/US2014/021970, mailed May 12, 2014.

* cited by examiner

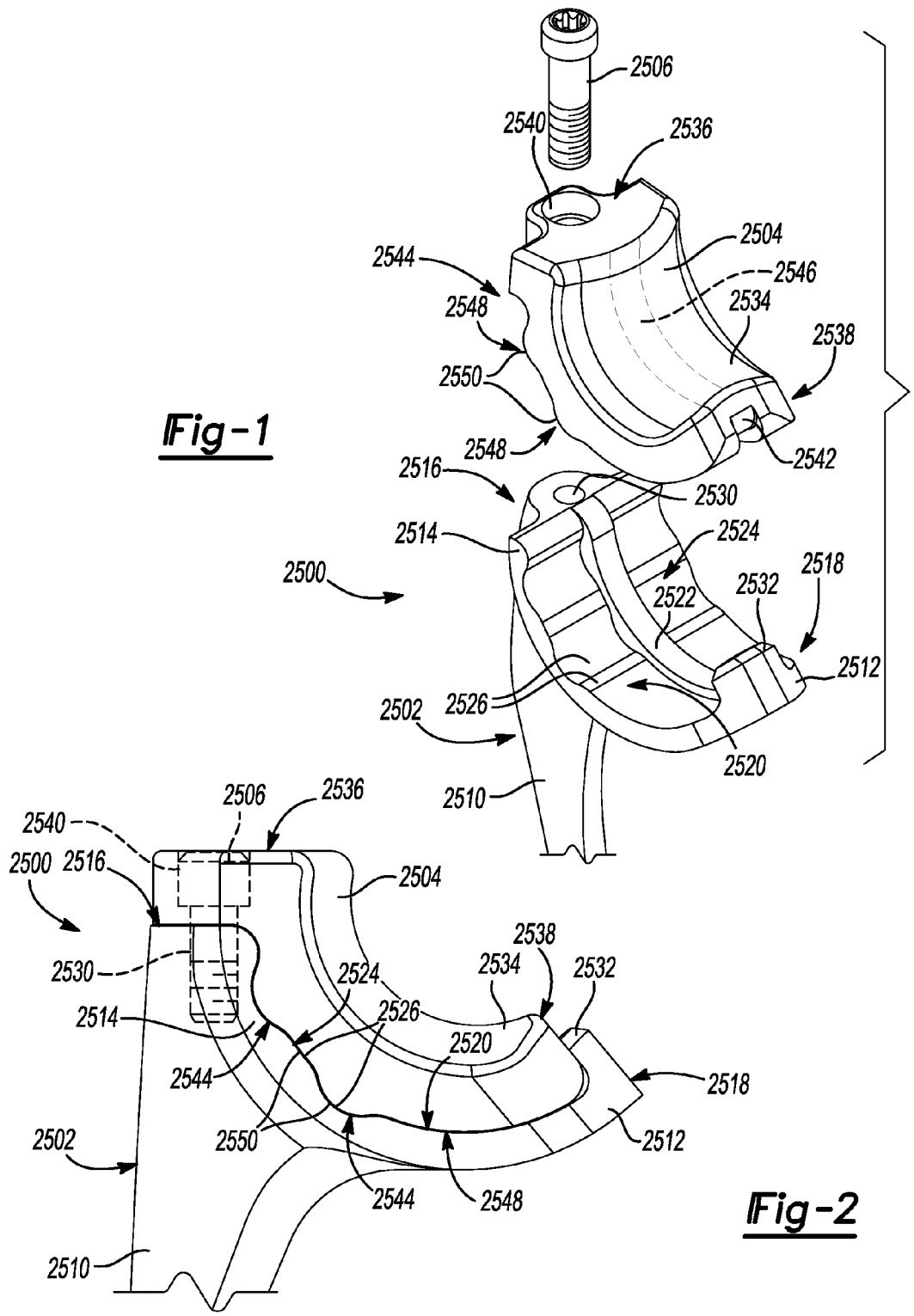

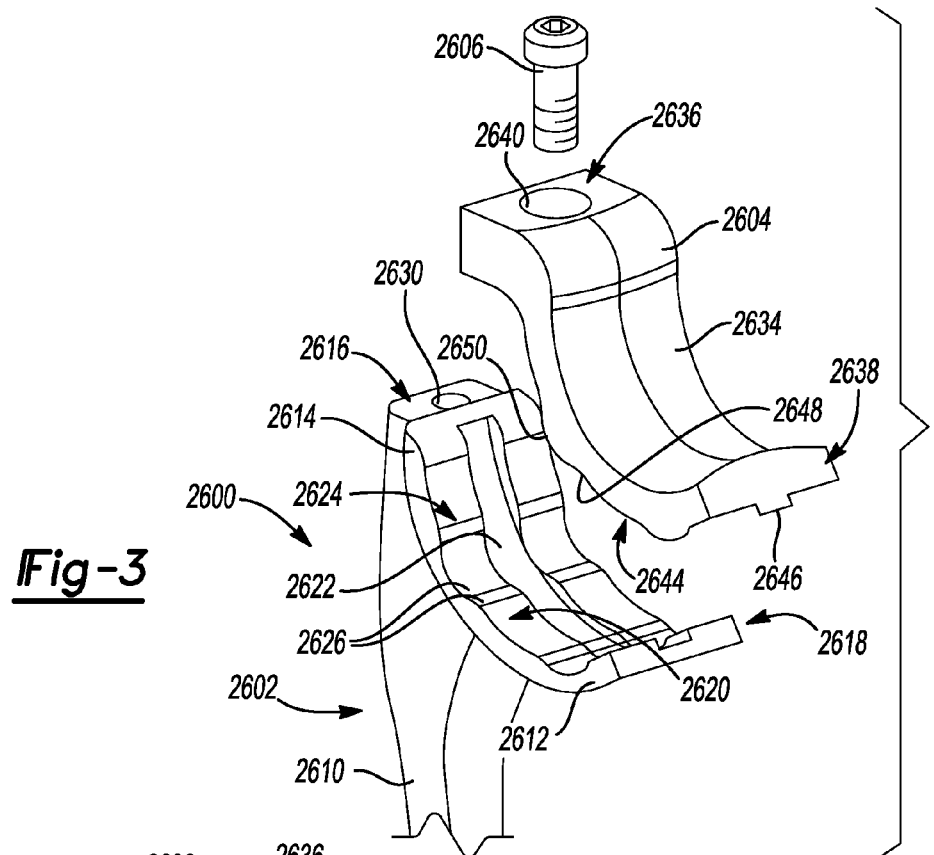
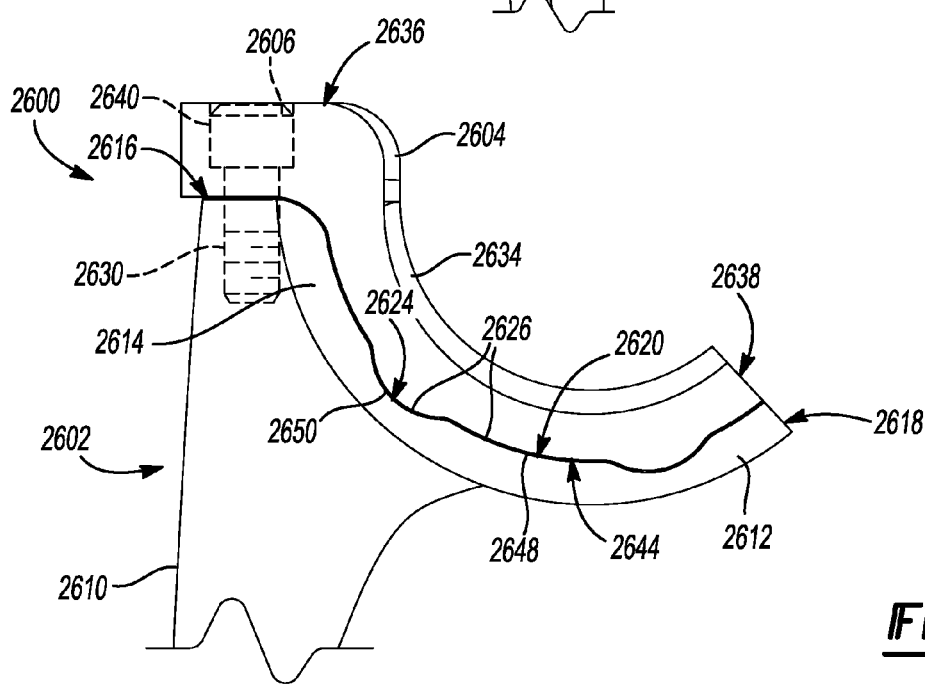

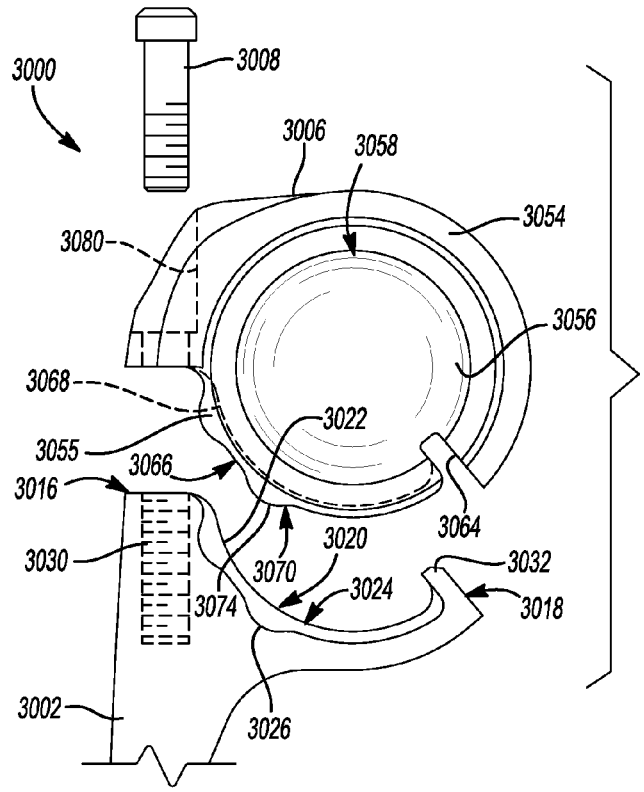
_Fig-9_
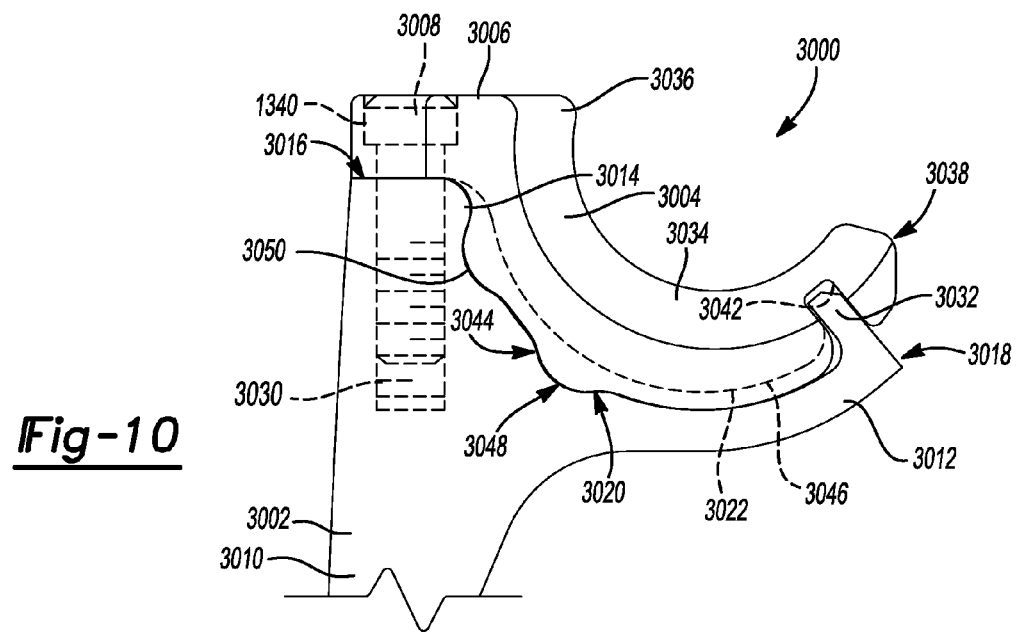
_Fig-10_

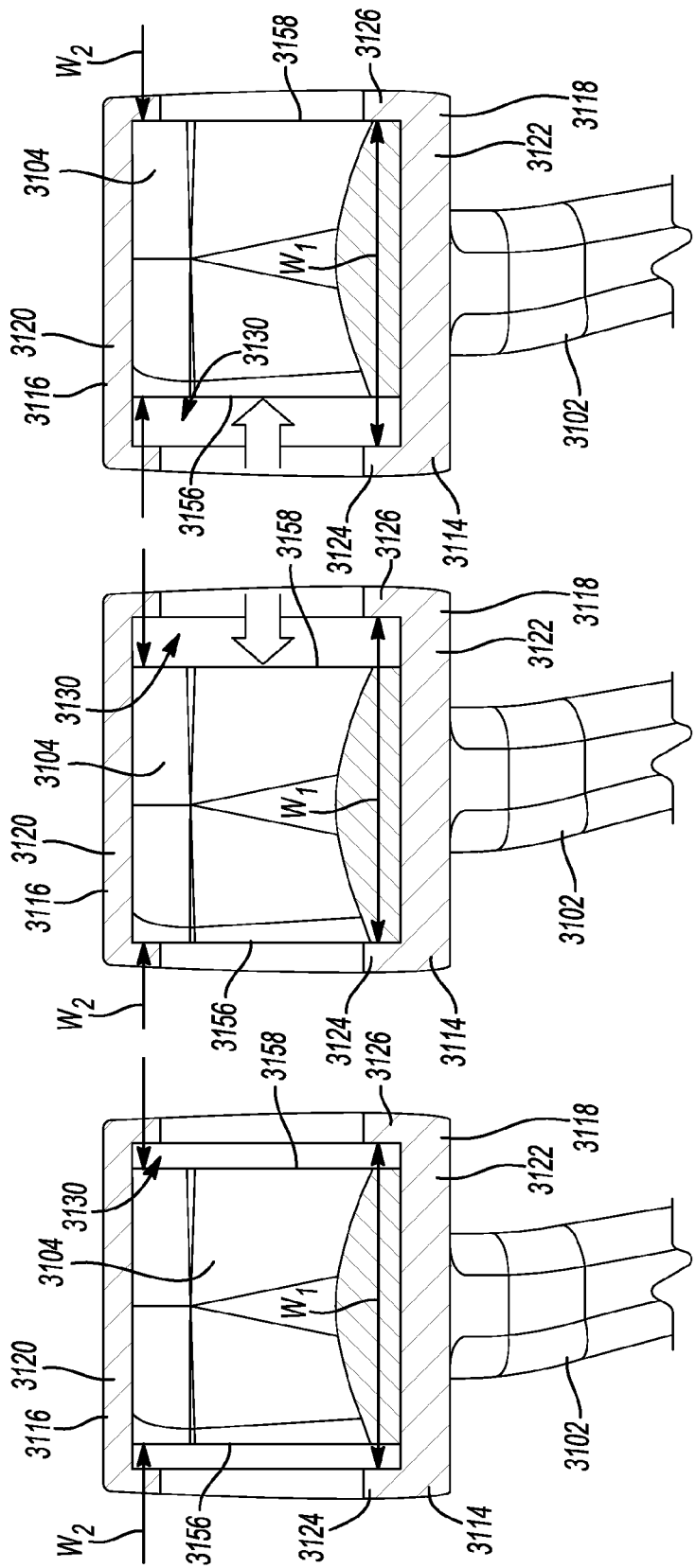

ELBOW PROSTHESIS

CROSS-REFERENCE TO RELATED APPLICATIONS

This application is a continuation-in-part of U.S. patent application Ser. No. 12/562,616, filed on Sep. 18, 2009, which is a continuation-in-part of U.S. patent application Ser. No. 12/391,904, filed on Feb. 24, 2009, which is a continuation-in-part of U.S. patent application Ser. No. 11/384,943 filed on Mar. 17, 2006, which is a continuation-in-part of U.S. patent application Ser. No. 10/333,140 filed on Jan. 15, 2003, which is a National Stage of International Application No. PCT/US01/22338 (published as WO 02/05728), filed Jul. 17, 2001, which claims priority to U.S. Provisional Application No. 60/219,103 filed Jul. 18, 2000. This application also claims priority to U.S. Provisional Application No. 61/505,360 filed on Jul. 7, 2011. Each of these applications are incorporated herein by reference.

U.S. patent application Ser. No. 11/780,365 filed on Sep. 19, 2007 which is now U.S. Pat. No. 7,625,406 and U.S. patent application Ser. No. 11/780,370 filed on Sep. 19, 2007 which is now U.S. Pat. No. 7,604,666 disclose related subject matter. These applications are also incorporated by reference.

FIELD

The present teachings relate generally to prosthetic devices used in arthroplasty and more particularly to a modular elbow prosthesis.

BACKGROUND

The present teachings relate generally to prosthetic devices used in arthroplasty and more particularly to a modular elbow prosthesis.

Linked or constrained elbow prostheses are known which comprise simple hinge arrangements, one component of which is attached to the end of the humerus and the other component of which is attached to the end of the ulna. The humeral component includes a shaft, which is cemented into a prepared cavity in the end of the humerus, and the ulnar component includes a shaft, that is cemented to the end of the ulna. The components of the prosthesis are connected together by means of a hinge pin so that the prosthesis allows a single degree of freedom of movement of the ulna relative to the humerus.

One example of a linked elbow prostheses is disclosed in U.S. Pat. No. 6,027,534 to Wack et al. In several respects, the linked embodiment of the '534 patent is typical of the designs for linked elbow prostheses in that it includes a humeral stem that terminates at a yoke at its distal end, a bearing component, a retaining pin and an ulna stem. The bearing component includes an oversized hole that is aligned with the longitudinal axis of the bearing and adapted to accept the retaining pin in a slip-fit condition. The distal end of the bearing component is coupled to the ulna stem. Despite the relatively widespread use of designs of this type, several drawbacks have been noted.

One significant drawback concerns the assembly of the elbow prosthesis after the surgeon has cemented the humeral and ulna stems to their respective bones. In using such conventionally configured linked elbow prosthesis devices, it is frequently necessary for the surgeon to drill a fairly large hole through the humerus so that the retaining pin may be inserted to the yoke of the humeral stem and the humeral bearing component. As a high degree of accuracy is typically required to ensure proper alignment between the hole in the humerus and the hole in the yoke of the humeral stem, a significant cost can be associated with this step in the installation of an elbow prosthesis due to the cost of the tooling used and the amount of time required to complete this step. The other method for attaching the prosthetic device includes inserting the device in its linked condition or placing the remaining piece into the yoke prior to fully seating the humeral component into the bone. This later method is typically somewhat difficult, given the limited amount of joint space that is available and the time constraints associated with the use of a PMMA bone cement.

Unlinked, or unconstrained, elbow prostheses are known which are similar to linked elbow prostheses but do not have a specific component which mechanically couples the humeral and ulnar stems together. Rather, the prosthetic device is held together by the patient's natural soft tissues. One example of an unlinked elbow prostheses is also disclosed in U.S. Pat. No. 6,027,534 to Wack et al. In several respects, the unlinked embodiment of the '534 patent is similar to the linked embodiment discussed above in that it includes a humeral stem that terminates at a yoke at its distal end, a humeral bearing component, a retaining pin, an ulnar bearing component and a ulnar stem. The outer surface of the humeral bearing is contoured to match the contour of the ulnar bearing component. Despite the relatively widespread use of designs of this type, several drawbacks have been noted.

For instance, a retaining pin that is transverse to the longitudinal axis of the patient is employed, thereby making its removal difficult if a bearing needs to be replaced.

SUMMARY

An elbow prosthesis according to the present teachings can include a stem structure and an articulating component. The stem structure can be operable to be positioned in a bone of a joint. The stem structure can include a stem portion that is operable to be positioned in the bone and a C-shaped body portion having a first retaining mechanism formed thereon. The articulating component can have a second retaining mechanism formed thereon. One of the first and second retaining mechanisms can comprise an extension portion and a first anti-rotation portion. The other retaining mechanism can comprise a receiving portion and a second anti-rotation portion. The articulating component can be advanced from an insertion position to an assembled position, such that the first and second mechanisms cooperatively interlock to inhibit translation and rotation of the articulating component relative to the C-shaped body portion of the stem structure.

According to other features, the extension portion can comprise a rail and the receiving portion can comprise a groove that receives the rail in the assembled position. The first anti-rotation portion can comprise a first wave-like pattern and the second anti-rotation portion can comprise a second wave-like pattern that cooperatively mates with the first wave-like pattern in the assembled position. The articulating component can comprise a bearing portion and the groove. The bearing portion can have the first end that defines a passage and a second end that includes a relief. The passage can be adapted to receive a fastener therethrough. The fastener can threadably couple the articulating component to the stem structure. The C-shaped body portion can include a catch that cooperatively nests in the relief of the bearing portion in the assembled position. A plurality of articulating components having various geometries can be provided.

An elbow prosthesis constructed in accordance to other features of the present teachings can include a tray structure, an articulating component and a securing member. The tray structure can be operable to be positioned in a bone of a joint. The tray structure can include a C-shaped body portion having a first retaining mechanism formed thereon and a boss portion extending from the C-shaped body portion a first distance. The boss portion can be operable to be positioned in the bone. The articulating component can have a second retaining mechanism formed thereon. The securing member can have a length that is greater than the first distance. The securing member can be adapted to be inserted into the boss such that a portion of a distal end of the securing member is advanced into the bone in an implanted position. The first and second retaining mechanisms can cooperatively interlock to inhibit movement of the articulating component relative to the C-shaped body portion in an assembled position.

According to additional features, the length of the securing member can be measured between terminal ends of the securing member. The boss portion can comprise a countersink portion and a shaft receiving portion. The countersink portion can have a larger diameter than the shaft receiving portion. The securing member can comprise a head portion and a threaded shank portion. The head portion can be configured to nest within the countersink portion and the threaded shank portion can be adapted to threadably advance into the bone in the implanted position.

According to still other features, one of the first and second retaining mechanisms can comprise an extension portion and a first anti-rotation portion. The other retaining mechanism can comprise a receiving portion and second anti-rotation portion. The articulating component can be advanced from an insertion position to an assembled position, such that the first and second retaining mechanisms cooperatively interlock to inhibit translation and rotation of the articulating component relative to the C-shaped body portion of the stem structure.

According to other features, an elbow prosthesis can comprise a stem structure, a first unlinked bearing component and a second linked bearing component. The stem structure can be operable to be positioned in a bone of a joint. The stem structure can include a stem portion operable to be positioned in the bone and an engaging portion extending from the stem portion. The first unlinked bearing component can have an exterior surface that opposes the engaging portion. The first unlinked bearing component can be selectively coupled to the engaging portion from an unassembled position to an assembled position. The second linked bearing component can have an exterior surface that opposes the engaging portion. The second linked bearing component can be selectively coupled to the engaging portion from an unassembled position to an assembled position. The first unlinked bearing component and the second linked bearing component can be selectively and alternatively coupled to the engaging portion of the stem portion.

According to additional features, the engaging portion can comprise a first retaining mechanism that cooperatively mates with a second retaining mechanism formed on either of the first unlinked bearing component or second linked bearing component.

According to additional features, an elbow prosthesis can comprise a stem structure and an articulating component. The stem structure can be operable to be positioned in a bone of a joint. The stem structure can include a stem portion and a C-shaped body portion. The stem portion can be operable to be positioned in the bone. The C-shaped body portion can have a first articulating surface that is bound by a medial wall and a lateral wall that are separated by a first distance. The articulating component can have a second articulating surface positioned between a medial side surface and a lateral side surface that are separated by a second distance. The first distance can be greater than the second distance. The second articulating surface of the articulating component can be configured to slidably communicate in a medial/lateral direction along the first articulating surface of the C-shaped body portion. The articulating component can be limited from further medial movement by engagement of the medial side surface with the medial wall and limited from further lateral movement by engagement of the lateral side surface with the lateral wall.

According to additional features, the C-shaped body portion can further include opposing walls that bound the articulating component from rotating around a medial/lateral axis. The elbow prosthesis can further comprise an unlinked humeral component that is configured to articulate with the articulating component. The unlinked humeral component can include a humeral articulating surface that opposes and articulates along a humeral opposing articulating surface of the articulating component. The humeral opposing articulating surface can include a first and second pair of diagonally opposed articulating surfaces. The humeral articulating surface can be configured to attain a first surface area contact with the first pair of diagonally opposed articulating surfaces in a varus position and attain a second surface area contact with the second pair of diagonally opposed articulating surfaces in a valgus position.

Further areas of applicability will become apparent from the description provided herein. It should be understood that the description and specific examples are intended for purposes of illustration only and are not intended to limit the scope of the present disclosure.

DRAWINGS

Additional advantages and features of the present teachings will become apparent from the subsequent description and the appended claims, taken in conjunction with the accompanying drawings, wherein:

FIG. 1 is a perspective view of a modular unlinked ulnar stem assembly constructed in accordance to one example of the present teachings;

FIG. 2 is an assembled view of the modular unlinked ulnar stem assembly of FIG. 1;

FIG. 3 is an exploded perspective view of another modular unlinked ulnar stem assembly constructed in accordance to the present teachings;

FIG. 4 is an assembled view of the modular unlinked ulnar stem assembly of FIG. 3;

FIG. 9 is an exploded medial side view a modular ulnar stem assembly that incorporates a universal stem and is shown with a linked bearing component;

FIG. 10 is a medial side assembled view of the modular unlinked ulnar stem assembly shown with an unlinked bearing component in an assembled position;

FIG. 16 is a cross-sectional view of the modular ulnar stem assembly taken along line 16 of FIG. 13 and shown with the mobile bearing in an intermediate position between a medial and lateral wall of the ulnar stem;

FIG. 17 is a cross-sectional view of the modular ulnar prosthesis of FIG. 13 and shown with the mobile bearing slidably translated into engagement with the medial wall of the ulnar prosthesis;

FIG. 18 is a cross-sectional view of the modular ulnar prosthesis of FIG. 13 and shown with the mobile bearing slidably translated into engagement with the lateral wall of the ulnar prosthesis;

DETAILED DESCRIPTION OF VARIOUS EMBODIMENTS

Figure 5:
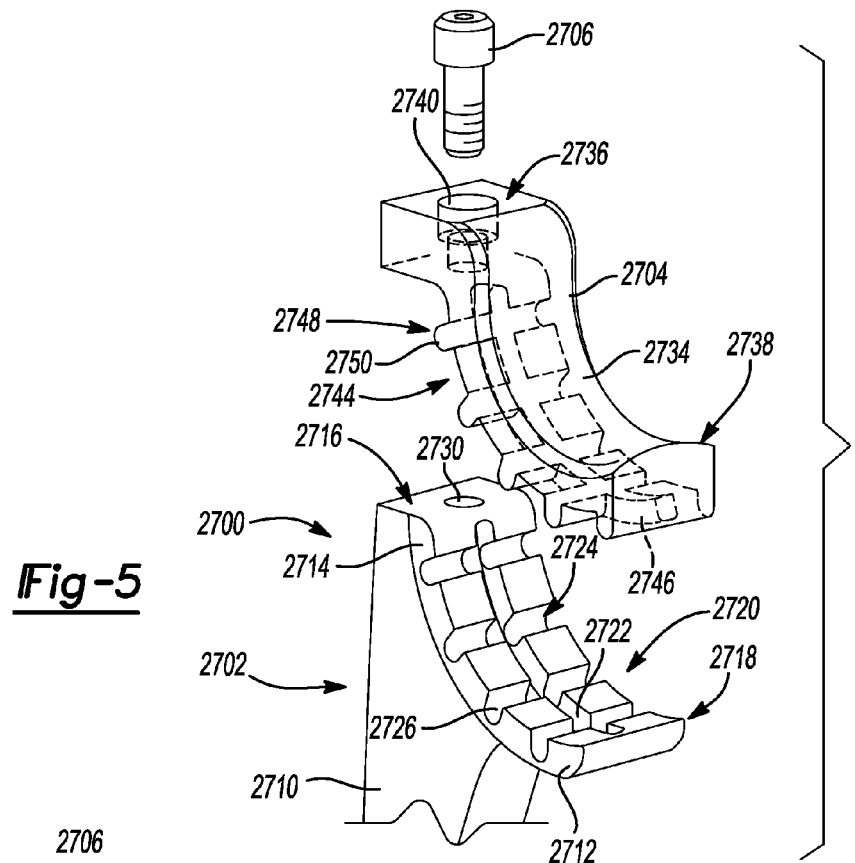
FIG. 5 is an exploded perspective view of another modular unlinked ulnar stem assembly constructed in accordance to the present teachings.

The following description is merely exemplary in nature and is not intended to limit the present disclosure, application, or uses. It should be understood that throughout the drawings, corresponding reference numerals indicate like or corresponding parts and features.

With reference to FIGS. 1, 2 and 3 of the drawings, an unlinked prosthetic joint device constructed in accordance with the teachings of a first aspect is generally indicated by reference number 2500. The following description is directed to various linked and unlinked prosthetic elbow joints. Additional features suitable for implementation with the following examples may be found in commonly owned and copending U.S. Ser. No. 12/780,424, filed May 14, 2010, which is expressly incorporated herein by reference. Although the particular prostheses illustrated and discussed relate to prosthetics for use in reconstructing an elbow, it will be understood that the teachings have applicability to other types of linked and unlinked prosthetic devices. As such, the scope of the present teachings will not be limited to applications involving elbow prosthesis but will extend to other prosthetic applications.

With reference now to FIGS. 1 and 2, a modular unlinked ulnar stem assembly 2500 constructed in accordance to one example of the present teachings will be described. In general, the modular unlinked ulnar stem assembly 2500 can include a stem structure 2502, an articulating component 2504 and a fastener 2506. As will become appreciated from the following discussion, the articulating component 2504 can be modular, such that a series or set of articulating components can be provided that are each selectively attachable to the stem structure 2502 according to a specific patient's needs. Such examples can include articulating components having different shapes, surfaces, sizes, constraints, etc. The modular unlinked ulnar stem assembly 2500 can be favorable in some circumstances as it has the potential to remove less native bone than other elbow prostheses, such as a semi-constrained total elbow, for example. Furthermore, the modular unlinked ulnar stem assembly 2500 can be favorable in circumstances where one side of the elbow joint includes satisfactory bone and/or cartilage and it is only desirable to replace the other side of the elbow joint.

With specific reference now to FIG. 1, exemplary features of the stem structure 2502 will be described. The stem structure 2502 can generally include a stem portion 2510 and a C-shaped body portion 2512. In this regard, the body portion 2512 can generally include an ulnar ring 2514 that is in the form of a partial or semi-circular cylinder. The body portion 2512 can generally extend between a first end 2516 and a second end 2518. The body portion 2512 can further comprise a first retaining mechanism 2520 formed thereon. The first retaining mechanism 2520 can include an extension portion 2522 and a first anti-rotation portion 2524. The extension portion 2522 can generally be in the form of a rail or keel that extends between the first end 2516 and the second end 2518 of the body portion 2512. The first anti-rotation portion 2524 can generally include a series of first undulations 2526 having a first series of peaks and valleys. In the example shown, the first undulations 2526 can be generally in the form of a wave-like pattern formed around the ulnar ring 2514. The specific geometry and wave-like pattern is merely exemplary and can consist of other formations that are configured to cooperatively engage complementary structure on the articulating component 2504 as will be described in detail herein.

The first end 2516 of the body portion 2512 can include a threaded bore 2530 formed therein. The second end 2518 of the body portion 2512 can include a catch 2532. As will be become appreciated from the following discussion, the first retaining mechanism 2520 that includes the first anti-rotation portion 2524 and the extension portion 2522 can cooperatively mate with complementary features formed on the articulating component 2504 and therefore inhibit rotation of the articulating component 2504 around the ulnar ring 2514 as well as inhibit medial/lateral translation of the articulating component 2504 on the ulnar ring 2514. The catch 2532 can also assist in confining the articulating component 2504 to a fixed position relative to the ulnar ring 2514. The configuration of the first retaining mechanism 2520 can be particularly advantageous during assembly of the articulating component 2504 onto the stem structure 2502 to maintain the articulating component 2504 in a static position relative to the ulnar ring 2514 prior to securing the articulating component 2504 further to the stem structure 2502 with the fastener 2506.

The articulating component 2504 will now be described in greater detail. In general, the articulating component 2504 can include a body 2534 that generally takes the shape of a partial or semi-circular cylinder complementary to the shape of the ulnar ring 2514. The body 2534 can extend between a first end 2536 and a second end 2538. The first end 2536 of the body 2534 can define a passage 2540 therein for receiving the fastener 2506 in the assembled position. The second end 2538 of the body 2534 can include a relief 2542. The articulating component 2504 can further comprise a second retaining mechanism 2544 that has a groove 2546 configured to receive the extension portion 2522 on the ulnar ring 2514 and a second anti-rotation portion 2548 for mating with the first anti-rotation portion 2524 on the ulnar ring 2514.

The second anti-rotation portion 2548 can include a series of second undulations 2550 having a second series of peaks and valleys that may be in the form of a wave-like pattern or other geometry that can suitably mate or nest with the first anti-rotating portion 2524 on the ulnar ring 2514. In one example, the articulating component 2504 can be formed of UHMWPE or PEEK. In other examples, however, the articulating component 2504 may be a combination of a first polyethylene portion on the articulating side and a molded metallic substrate that forms the second anti-rotation portion 2548. The molded configuration can be similar to the combination polyethylene and metallic component described in pending U.S. Ser. No. 12/780,424, filed May 14, 2010 identified above.

With specific reference to FIG. 2, assembly of the articulating component 2504 to the stem structure 2502 according to one example of the present teachings will be described. At the outset, a surgeon can advance the second retaining mechanism 2544 of the articulating component 2504 onto the first retaining mechanism 2520 of the stem structure 2502. In this regard, the second anti-rotation portion 2548 can cooperatively mate with the first anti-rotation portion 2524 as the extension portion 2522 of the first retaining mechanism 2520 nests within the groove 2546 of the second retaining mechanism 2544. At this time, the catch 2534 on the ulnar ring 2514 can locate partially into the relief 2542 of the articulating component 2504. Those skilled in the art will readily appreciate that the cooperatively mating structures formed on the stem structure 2502 and the articulating component 2504 may be reversed. For example, the extension portion 2522 may alternatively be provided on the articulating component 2504 while the groove 2546 may alternatively be located on the body portion 2512 of the stem structure 2502. Likewise, the catch 2532 and the relief 2542 may be provided on opposite components.

Nonetheless, once the first and second retaining mechanisms 2520 and 2544 have been positioned against each other (FIG. 2), translation of the articulating component 2504 in the medial/lateral direction can be inhibited by the interaction of the extension portion 2522 and the groove 2546. Likewise, rotation of the articulating component 2504 around the ulnar ring 2514 can be inhibited by the interaction of the first and second anti-rotation portions 2524 and 2548. The catch 2532 can assist in further inhibiting rotational movement of the articulating component 2504. Moreover, as the catch 2532 is angled toward the second end 2538 of the articulating component 2504, the articulating component 2504 can be inhibited from lift-off from the stem structure 2502. Next, the fastener 2506 can be advanced through the passage 2540 in the articulating component 2504 and threadably advanced into the threaded bore 2530 of the stem portion 2510 to couple the articulating component 2504 to the stem portion 2510.

Turning now to FIGS. 3 and 4, another modular unlinked ulnar stem assembly 2600 according to the present teachings will be described. In general, the modular unlinked ulnar stem assembly 2600 can include a stem structure 2602, an articulating component 2604 and a fastener 2606. The stem structure 2602 can generally comprise a stem portion 2610 and a generally C-shaped body portion 2612. The stem structure 2602 can generally include an ulnar ring 2614 that is in the form of a partial or semi-circular cylinder. The ulnar ring 2614 can generally extend between a first end 2616 and a second end 2618. The body portion 2612 can further comprise a first retaining mechanism 2620. The first retaining mechanism 2620 can include a groove 2622 and a first anti-rotation portion 2624. The first anti-rotation portion 2624 can be in the form of first undulations 2626. A threaded bore 2630 can be formed on the stem structure 2602 at the first end 2616 of the body portion 2612.

The articulating component 2604 will now be further described according to one example. The articulating component 2604 can be modular, such that a series of articulating components can be provided that are selectively attachable to the stem structure 2602 according to a specific patient's needs. In general, the articulating component 2604 can include a body 2634 that generally takes the shape of a partial or semi-circular cylinder complementary to the shape of the ulnar ring 2614. The body 2634 can generally extend between a first end 2636 and a second end 2638. The body 2634 can define a passage 2640 configured to receive the fastener 2606 at the first end 2636. The articulating component 2604 can further comprise a second retaining mechanism 2644 that can comprise an extension portion 2646 in the form of a rail or keel and a second anti-rotation portion 2648. The second anti-rotation portion 2648 can be in the form of a series of second undulations 2650 that are provided with a geometry suitable to cooperatively mate or nest with the first undulations 2626 of the first anti-rotation portion 2624. Again, it will be appreciated that the configuration and location of some or all of the various structures of the first and second retaining mechanisms 2620 and 2644 can be swapped between components. In one example, the articulating component 2604 can be formed of UHMWPE or PEEK. In other examples, however, the articulating component 2604 may be a combination of a first polyethylene portion on the articulating side and a molded metallic substrate that forms the second anti-rotation portion 2648. The molded configuration can be similar to the combination polyethylene and metallic component described in pending U.S. Ser. No. 12/780,424, filed May 14, 2010 identified above.

Assembly of the articulating component 2604 to the stem structure 2602 will now be described according to one example. Initially, a surgeon can locate the second retaining mechanism 2644 onto the first retaining mechanism 2620. In this regard, the extension portion 2646 can be nestingly received by the groove 2622 on the body portion 2612 of the stem structure 2602. Concurrently, the second undulations 2650 on the second anti-rotation portion 2648 can be matingly engaged with the first undulations 2626 of the first anti-rotation portion 2624. Again, the interaction of the extension portion 2646 and the groove 2622 can inhibit medial/lateral translation of the articulating component 2604 relative to the stem structure 2602. Similarly, the interaction of the first and second anti-rotation portions 2624 and 2648 can inhibit rotation of the articulating component 2604 around the body 2612 of the stem structure 2602. Next, the fastener 2606 can be advanced through the passage 2640 and threadably mated into the threaded bore 2630 of the stem structure 2602 to couple the articulating component 2604 to the stem structure 2602.

Figure 6:
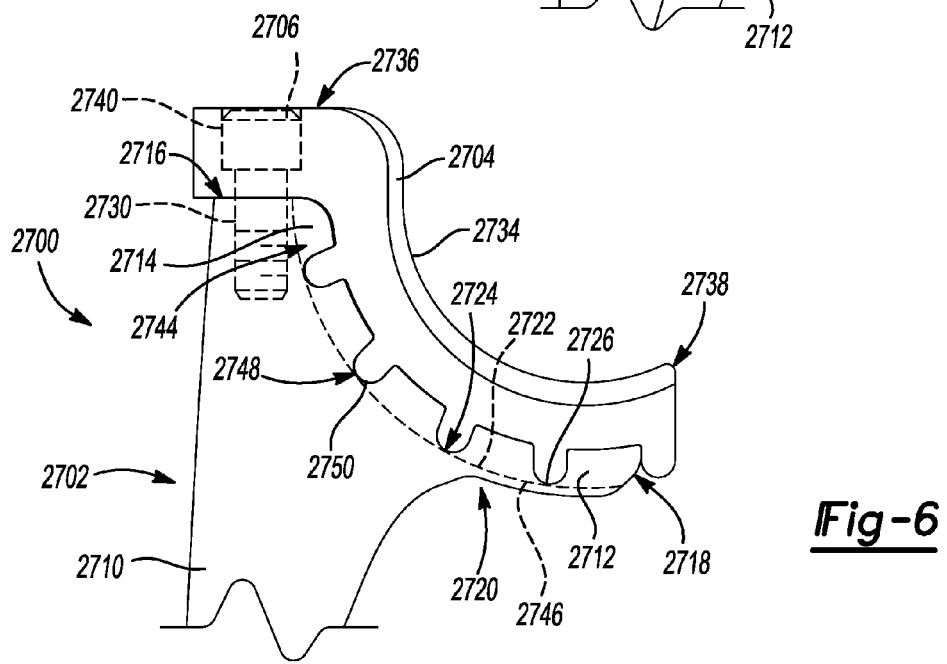
FIG. 6 is an assembled view of the modular unlinked ulnar stem assembly of FIG. 5.

Turning now to FIGS. 5 and 6, another modular unlinked ulnar stem assembly 2700 according to the present teachings will now be described. In general, the modular unlinked ulnar stem assembly 2700 can include a stem structure 2702, an articulating component 2704 and a fastener 2706. Again, as with the other examples discussed herein, the articulating component 2704 can be modular, such that a series of articulating components having various geometries can be provided that are selectively attachable to the stem structure 2702 according to a specific patient's needs. The stem structure 2702 can include a stem portion 2710 and a body portion 2712. The body portion 2712 can be in the form of an ulnar ring 2714 that extends between a first end 2716 and a second end 2718. The body portion 2712 can comprise a first retaining mechanism 2720 that can include a groove 2722 and a first anti-rotation portion 2724. The first anti-rotation portion 2724 can be in the form of a series of depressions 2726. In one example, the depressions 2726 can be perpendicular to the groove 2722. The body portion 2712 can include a threaded bore 2730 formed at the first end 2516.

The articulating component 2704 can include a body 2734 that generally takes the shape of a partial or semi-circular cylinder complementary to the shape of the ulnar ring 2714. The body 2734 can extend between a first end 2736 and a second end 2738. The articulating component 2704 can further define a passage 2740 formed therethrough at the first end 2736 for receiving the fastener 2706. The articulating component 2704 can further comprise a second retaining mechanism 2744 that can include an extension portion 2746 and a second anti-rotation portion 2748. The second anti-rotation portion 2748 can be in the form of a series of fingers 2750 that are shaped to be cooperatively received into the depressions 2726 of the first retaining mechanism 2720. In one example, the extension portion 2746 can be perpendicular to the fingers 2750. Again, it is appreciated that some or all of the features of the first and second retaining mechanisms 2720 and 2744 can be swapped between the stem structure 2702 and the articulating component 2704. Moreover, while the number of depressions 2726 shown around the ulnar ring 2714 is four, fewer or additional depressions 2726 may be used for cooperatively mating with a like amount of fingers 2750. Additionally, some or all features of the second retaining mechanism 2744 on the articulating component 2704 can be formed of a metallic material while the remainder of the articulating component 2704 can be formed of UHMWPE.

Assembly of the articulating component 2704 with the stem portion 2710 will now be described. Initially, a surgeon can locate the second retaining mechanism 2744 of the articulating component 2704 onto the first retaining mechanism 2720 of the stem structure 2702. In this regard, the extension portion 2746 and the fingers 2750 can cooperatively nest into the groove 2722 and depressions 2726, respectively. As with the other examples described above, the interaction of the extension portion 2746 and the groove 2722 can inhibit medial/lateral translation of the articulating component 2704 relative to the stem structure 2702. Similarly, interaction of the fingers 2750 and the depressions 2726 can inhibit rotation of the articulating component 2704 around the ulnar ring 2714. Next, the fastener 2706 can be located through the passage 2740 and threadably advanced into the threaded bore 2730 of the stem portion 2710.

Figure 7:
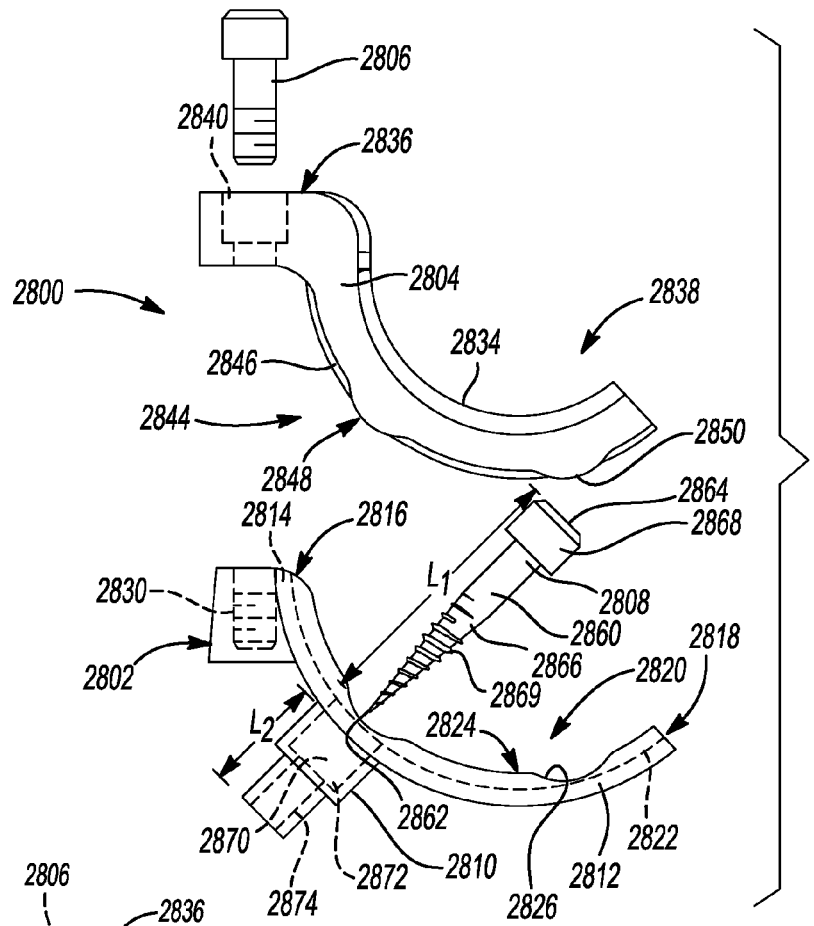
FIG. 7 is an exploded medial side view of a stemless modular unlinked ulnar prosthesis according to the present teachings.
Figure 8:
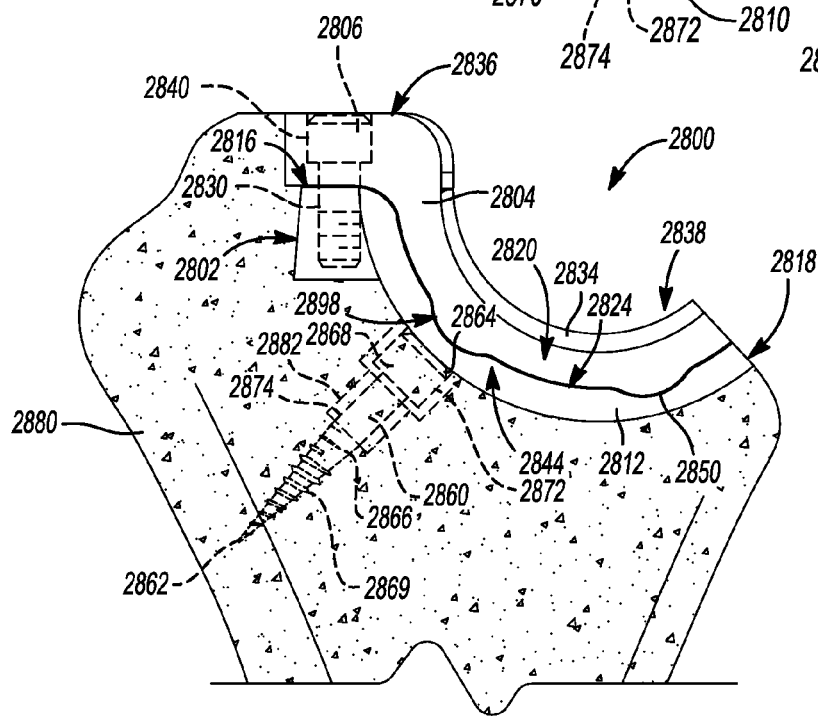
FIG. 8 is a medial side view of the stemless modular unlinked ulnar prosthesis shown in FIG. 7 and implanted into an ulna.

With reference now to FIGS. 7 and 8, a modular unlinked ulnar prosthesis assembly 2800 constructed in accordance to one example of the present teachings will be described. In general, the modular unlinked ulnar prosthesis assembly 2800 can include a tray structure 2802, an articulating component 2804, a fastener 2806 and a securing member 2808. As will become appreciated from the following discussion, the articulating component 2804 can be modular, such that a series of articulating components can be provided that are each selectively attachable to the tray structure 2802 according to a specific patient's needs. The modular unlinked ulnar prosthesis assembly 2800 can be favorable in some circumstances as it has the potential to remove less native bone than other elbow prostheses, such as a semi-constrained total elbow, for example. Moreover, the modular unlinked ulnar prosthesis assembly 2800 has the potential to remove less native bone than other unlinked ulnar prosthesis assemblies that require the use of a stem, such as disclosed herein. In this regard, the modular unlinked ulnar prosthesis assembly 2800 can be referred to as a "stemless" ulnar prosthesis as the only structure that ultimately is required to penetrate into the native bone is a boss portion 2810 and related securing member 2808 as will be discussed in greater detail. As such, a conventional stem that may be configured to pass into an IM canal of the ulna is not required for the modular unlinked ulnar prosthesis assembly 2800. As with some of the modular unlinked ulnar prostheses discussed above, the modular unlinked ulnar prosthesis assembly 2800 can be favorable in circumstances where one side of the elbow joint includes satisfactory bone and/or cartilage and it is only desirable to replace the other side of the elbow joint.

With specific reference now to FIG. 7, exemplary features of the tray structure 2802 will be described. The tray structure 2802 can generally include a boss portion 2810 and a C-shaped body portion 2812. In this regard, the body portion 2812 can generally include an ulnar ring 2814 that is in the form of a partial or semi-circular cylinder. The body portion 2812 can generally extend between a first end 2816 and a second end 2818. The body portion 2812 can further comprise a first retaining mechanism 2820 formed thereon. The first retaining mechanism 2820 can include a receiving portion or arcuate groove 2822 and a first anti-rotation portion 2824. The groove 2822 can generally be in the form of a centrally positioned channel that extends between the first end 2816 and the second end 2818 of the body portion 2812. The first anti-rotation portion 2824 can generally include a series of first undulations 2826. In the example shown, the first undulations 2826 can be generally in the form of a wave-like pattern formed around the ulnar ring 2814 and project perpendicular to the groove 2822. The specific geometry and wave-like pattern is merely exemplary and can consist of other formations that are configured to cooperatively engage complementary structure on the articulating component 2804 as will be described in detail herein.

The first end 2816 of the body portion 2812 can include a threaded bore 2830 therein. As will become appreciated from the following discussion, the first retaining mechanism 2820 that includes the first anti-rotation portion 2824 and the groove 2822 can cooperatively mate with complementary features formed on the articulating component 2804 and therefore inhibit rotation of the articulating component 2804 around the ulnar ring 2814 as well as inhibit medial/lateral translation of the articulating component 2804 on the ulnar ring 2814. The configuration of the first retaining mechanism 2820 can be particularly advantageous during assembly of the articulating component 2804 onto the tray structure 2802 to maintain the articulating component 2804 in a static position relative to the ulnar ring 2814 prior to securing the articulating component 2804 further to the tray structure 2802 with the fastener 2806.

The articulating component 2804 will now be described in greater detail. In general, the articulating component 2804 can include a body 2834 that generally takes the shape of a partial or semi-circular cylinder complementary to the shape of the ulnar ring 2814. The body 2834 can extend between a first end 2836 and a second end 2838. The first end 2836 of the body 2834 can define a passage 2840 therein for receiving the fastener 2806 in the assembled position (FIG. 8). The articulating component 2804 can further comprise a second retaining mechanism 2844 that has an arcuate keel or extension portion 2846 configured to be nestingly received into the groove 2822 on the ulnar ring 2814. Similarly, the second retaining mechanism 2844 can also include a second anti-rotation portion 2848 for mating with the first anti-rotation portion 2824 on the ulnar ring 2814. The second anti-rotation portion 2848 can include a series of second undulations 2850 that may be in the form of a wave-like pattern or other geometry that can suitably mate with the first anti-rotation portion 2824 on the ulnar ring 2814. The keel 2846 can extend generally perpendicular to the second undulations 2850. In one example, the articulating component 2804 can be formed of UHMWPE or PEEK. In other examples, however, the articulating component 2804 may be a combination of a first polyethylene portion on the articulating side and a molded metallic substrate that forms the second anti-rotation portion 2848. The molded configuration can be similar to the combination polyethylene and metallic component described in pending U.S. Ser. No. 12/780,424, filed May 14, 2010 described above.

The securing member 2808 will now be described in greater detail. In general, the securing member 2808 can include a body 2860 that extends between a first terminal end 2862 and a second terminal end 2864. The body 2860 can have a shank 2866 and a head 2868. At least portions of the shank 2866, initiating at the first terminal end 2862 can have threads 2869 formed thereon. The securing member 2808 can extend a length $L_1$ between the respective first and second terminal ends 2862 and 2864.

Additional features of the boss portion 2810 of the tray structure 2802 will be described. The boss portion 2810 can have a bore 2870 that has a countersink 2872 and a shaft receiving portion 2874. The boss portion 2810 can have a length $L_2$ that extends from the body portion 2812 of the tray structure 2802 to a terminal end of the boss portion 2810. The boss portion 2810 can be roughened, porous coated and/or plasma sprayed to facilitate boney ingrowth.

Locating the tray structure 2802 relative to an ulna 2880 according to one example will now be described. In some examples, the ulna 2880 may be minimally reamed to create a counterbore 2882 for receipt of the boss portion 2810. Nevertheless, once the ulna 2880 has been suitably prepared for receipt of the tray structure 2802, the tray structure 2802 can be located onto the ulna 2880 to resurface the ulna 2880. Next, the surgeon can select the securing member 2808 and pass the shank 2866 into the bore 2870 formed in the boss portion 2810 of the tray structure 2802. It will be appreciated that a plurality of distinct length securing members may be provided such that a surgeon can select an appropriate length according to the application.

The surgeon can then threadably advance the securing member 2808 into the ulna 2880 until the head 2868 can locate into the countersink 2872 while the shank 2866 is received through the shaft receiving portion 2874 of the boss portion 2810. In this regard, because the length $L_1$ of the securing member 2808 is greater than the length $L_2$ of the boss portion 2810, at least a portion of the shank 2866 having the threads 2869 can extend proud through the boss portion 2810 and into the host ulna 2880. Preferably, the head 2868 can be advanced to a distance where the second terminal end 2864 of the securing member 2808 is at least flush with or recessed into the countersink 2872 of the boss portion 2810 so as not to interfere with the articulating component 2804.

With continued reference to FIGS. 7 and 8, assembly of the articulating component 2804 to the tray structure 2802 according to one example of the present teachings will be described. At the outset, a surgeon can advance the second retaining mechanism 2844 of the articulating component 2804 onto the first retaining mechanism 2820 of the tray structure 2802. In this regard, the second anti-rotation portion 2848 can cooperatively mate with the first anti-rotation portion 2824 as the extension portion 2846 of the second retaining mechanism 2844 nests within the groove 2822 of the first retaining mechanism 2820. Again, those skilled in the art will readily appreciate that some or all of the cooperatively mating structure formed on the tray structure 2802 and the articulating component 2804 may be reversed. Once the first and second retaining mechanisms 2820 and 2844 have been positioned against each other, translation of the articulating component 2804 and the medial/lateral direction can be inhibited by the interaction of the extension portion 2846 and the groove 2822. Likewise, rotation of the articulating component 2804 around the ulnar ring 2814 can be inhibited by the interaction of the first and second anti-rotation portions 2824 and 2848.

Figure 11:
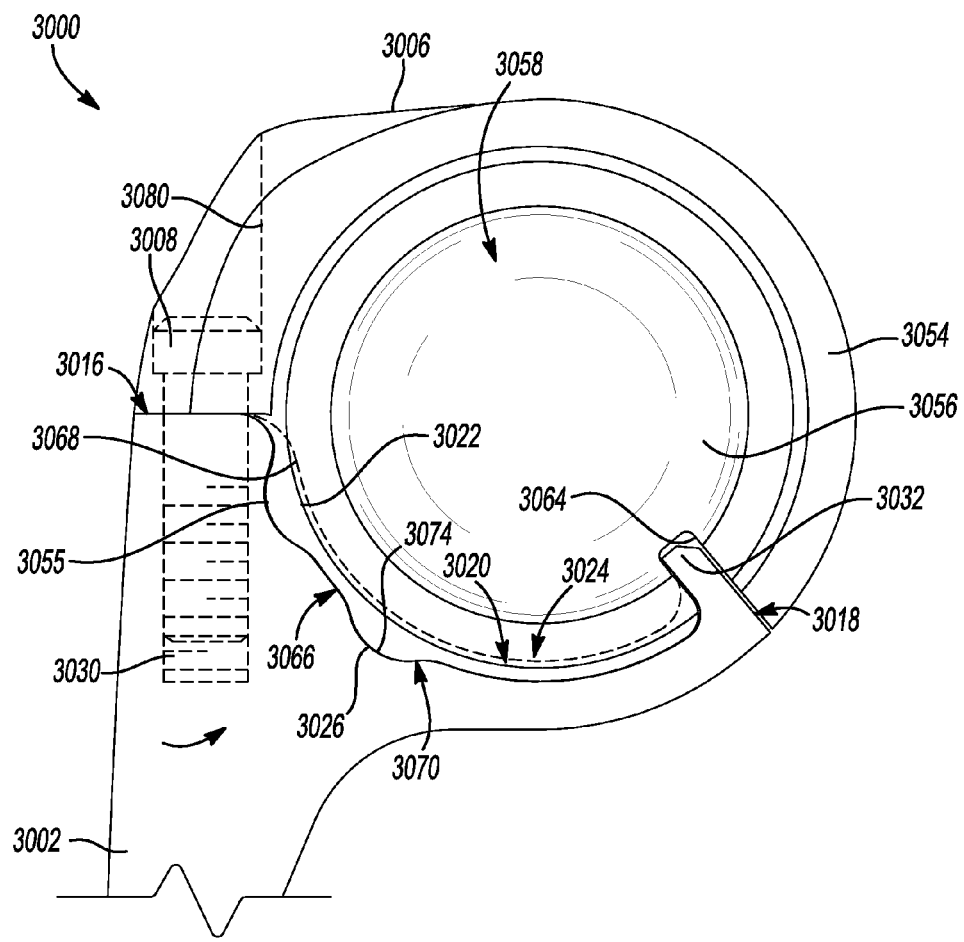
FIG. 11 is a medial side assembled view of the modular ulnar stem assembly of FIG. 9 shown with the linked bearing component secured to the universal stem.

With reference now to FIGS. 9-11, a modular ulnar stem assembly 3000 constructed in accordance to one example of the present teachings will be described. In general, the modular ulnar stem assembly 3000 can include a universal stem structure 3002, an unlinked bearing component 3004 (FIG. 10), a linked bearing component 3006 (FIG. 9) and a fastener 3008. As will be described herein, the universal stem 3002 can be configured to selectively and alternatively couple with either of the unlinked bearing component 3004 or the linked bearing component 3006. In this regard, in some instances where a patient may have the universal stem 3002 implanted with the unlinked bearing component 3004 and, over time, it may become desirable to convert the prosthesis to a configuration having a linked bearing component, a surgeon can access the elbow and merely replace the unlinked bearing component 3004 with a linked bearing component 3006. In doing so, the surgeon need not substantially disturb the universal stem 3002 as it is configured to selectively and alternatively couple with either of the unlinked bearing component 3004 and the linked bearing component 3006. As with the other modular ulnar assemblies described herein, the unlinked bearing component 3004 and the linked bearing component 3006 can both be modular, such that a series of unlinked and linked bearing components can be provided that are each selectively attachable to the universal stem 3002 according to specific patient's needs.

With specific reference now to FIGS. 9 and 10, exemplary features of the universal stem 3002 will be described. The universal stem 3002 can generally include a stem portion 3010 and a C-shaped body portion 3012. In this regard, the body portion 3012 can generally include an ulnar ring 3014 that is in the form of a partial or semi-circular cylinder. The body portion 3012 can generally extend between a first end 3016 and a second end 3018. The body portion 3012 can further comprise a first retaining mechanism 3020 thereon. The first retaining mechanism 3020 can include an extension portion 3022 and a first anti-rotation portion 3024. The extension portion 3022 can generally be in the form of an arcuate rail or keel that centrally extends between the first end 3016 and the second end 3018 of the body portion 3012. The first anti-rotation portion 3024 can generally include a series of first undulations 3026. In the example shown, the first undulations 3026 can be generally in the form of a wave-like pattern formed around the ulnar ring 3014. The specific geometry and wave-like pattern is merely exemplary and can consist of other formations that are configured to cooperatively engage complementary structure on either of the unlinked bearing component 3004 and the linked bearing component 3006 as will be described in detail herein.

The first end 3016 of the body portion 3012 can include a threaded bore 3030 formed therein. The second end 3018 of the body portion 3012 can include a catch 3032. As will become appreciated from the following discussion, the first retaining mechanism 3020 that includes the first anti-rotation portion 3024 and the extension portion 3022 can cooperatively mate with complementary features formed on either of the unlinked bearing component 3004 or the linked bearing component 3006. In this regard, the cooperating geometries can therefore inhibit rotation of the unlinked bearing component 3004 (or the linked bearing component 3006) around the ulnar ring 3014, as well as inhibit medial/lateral translation of the unlinked bearing component 3004 (or the linked bearing component 3006) on the ulnar ring 3014. Both ends of the linked bearing component 3006 can therefore be positively secured to the universal stem 3002. The catch 3032 can also assist in confining the unlinked bearing component 3004 or the linked bearing component 3006 to a fixed position relative to the ulnar ring 3014. The configuration of the first retaining mechanism 3020 can be particularly advantageous during assembly of either of the unlinked bearing component 3004 or the linked bearing component 3006 onto the universal stem 3002. For example, the first retaining mechanism 3020 can maintain the respective unlinked or linked bearing components 3004 and 3006 in a static position relative to the ulnar ring 3014 prior to securing the respective unlinked or linked bearing components 3004 and 3006 further to the universal stem 3002 with the fastener 3008.

The unlinked bearing component 3004 will now be described in greater detail. In general, the unlinked bearing component 3004 can include a body 3034 that generally takes the shape of a partial or semi-circular cylinder complementary to the shape of the ulnar ring 3014. The body 3034 can extend between a first end 3036 and a second end 3038. The first end 3036 of the body 3034 can define a passage 3040 therein for receiving the fastener 3008 in the assembled position (FIG. 10). The second end 3038 of the body 3034 can include a notch or relief 3042. The unlinked bearing component 3004 can further comprise a second retaining mechanism 3044 that has a groove 3046 configured to receive the extension portion 3022 on the ulnar ring 3014 and a second anti-rotation portion 3048 for cooperatively mating with the first anti-rotation portion 3024 on the ulnar ring 3014.

The second anti-rotation portion 3048 can include a series of second undulations 3050 that may be in the form of a wave-like pattern or other geometry that can suitably mate with the first anti-rotation portion 3024 on the ulnar ring 3014. The second undulations 3050 can be perpendicular to the groove 3046. In one example, the unlinked bearing component 3004 can be formed of UHMWPE or PEEK. In other examples, however, the unlinked bearing component 3004 may be a combination of a first polyethylene portion on the articulating side and a molded metallic substrate that forms the second anti-rotation portion 3048. The molded configuration can be similar to the combination of polyethylene and metallic component described in pending U.S. Ser. No. 12/780,424, filed May 14, 2010 described above.

With specific reference now to FIG. 10, assembly of the unlinked bearing component 3004 to the universal stem 3002 according to one example of the present teachings will be described. At the outset, a surgeon can advance the second retaining mechanism 3044 of the unlinked bearing component 3004 onto the first retaining mechanism 3020 of the universal stem 3002. In this regard, the second anti-rotation portion 3048 can cooperatively mate with the first anti-rotation portion 3024 as the extension portion 3022 of the first retaining mechanism 3020 nests within the groove 3046 of the second retaining mechanism 3044. At this time, the catch 3032 on the ulnar ring 3014 can locate partially into the relief 3042 of the unlinked bearing component 3004. Those skilled in the art will readily appreciate that the cooperatively mating structures formed on the universal stem 3002 and the unlinked bearing component 3004 may be reversed. For example, the extension portion 3022 may alternately be provided on the unlinked bearing component 3004 (and the linked bearing component 3006) while the groove 3046 may alternatively be located on the body portion 3012 of the universal stem 3002. Likewise, the catch 3032 and the relief 3042 may be provided on opposite components.

Nonetheless, once the first and second retaining mechanisms 3020 and 3044 have been positioned against each other, translation of the unlinked bearing component 3004 in the medial/lateral direction can be inhibited by the interaction of the extension portion 3022 and the groove 3046. Likewise, rotation of the unlinked bearing component 3004 around the ulnar ring 3014 can be inhibited by the interaction of the first and second anti-rotation portions 3024 and 3048. The catch 3032 can assist in further inhibiting rotational movement of the unlinked bearing component 3004. Next, the fastener 3008 can be advanced through the passage 3040 in the unlinked bearing component 3004 and threadably advanced into the threaded bore 3030 of the stem portion 3010 to further secure the unlinked bearing component 3004 to the stem portion 3010.

With specific reference now to FIG. 9, the linked bearing component 3006 will be described in greater detail. In general, the linked bearing component 3006 can include a substrate or body 3054 that generally takes the shape of a closed ring that has a mating portion 3055 that is complementary to the shape of the ulnar ring 3014. The body 3054 can generally include a bearing portion 3056 that is molded to the body 3054. The bearing portion 3056 can have a closed bearing surface 3058. The body 3054 can further include a notch or relief 3064 and retaining mechanism 3066 that has a groove 3068 configured to receive the extension portion 3022 of the universal stem 3002 and a second anti-rotation portion 3070 configured to mate with the first anti-rotation portion 3024 on the ulnar ring 3014.

The second retaining mechanism 3066 can include a series of second undulations 3074 that may be in the form of a wave-like pattern or other geometry that can suitably mate with the first anti-rotation portion 3024 on the ulnar ring 3014. In one example, the bearing portion 3056 can be formed of UHMWPE or PEEK that is molded over the body 3054. The remainder of the body 3054, such as including the mating portion 3055, can be formed of a metallic substrate that can encompass the bearing portion 3056. The body 3054 can include a passage 3080 therein for receiving the fastener 3008 in the assembled position (see FIG. 11).

With reference now to FIGS. 9 and 11, assembly of the linked bearing component 3006 to the universal stem 3002 according to one example of the present teachings will be described. Again, it will be appreciated that it may be desirable to replace the unlinked bearing component 3004 with a linked bearing component 3006 to provide increased constraint. At the outset, a surgeon may remove the unlinked bearing component 3004 from the universal stem 3002. In this regard, the fastener 3008 can be threadably retracted from the threaded bore 3030 and the universal stem 3002 and the unlinked bearing component 3004 subsequently removed from the universal stem 3002. It will be appreciated that in other examples, a surgeon can intra-operatively decide whether to select the unlinked bearing component 3004 or the linked bearing component 3006 based on a given patient.

Once the unlinked bearing component 3004 has been suitably removed, the linked bearing component 3006 can be coupled to the universal stem 3002. Again, as with the other embodiments described herein, a linked bearing component 3006 can be selected from a plurality of linked bearing components according to the needs of a particular patient. The surgeon can advance the second retaining mechanism 3066 of the linked bearing component 3006 onto the first retaining mechanism 3020 of the universal stem 3002. In this regard, the second anti-rotation portion 3070 can cooperatively mate with the first anti-rotation portion 3024 as the extension portion 3022 of the first retaining mechanism 3020 nests within the groove 3068 of the second retaining mechanism 3066. At this time, the catch 3032 on the ulnar ring 3014 can locate partially into the notch 3064 of the linked bearing component 3006. Those skilled in the art will readily appreciate that the cooperatively mating structure is formed on the universal stem 3002 and the linked bearing component 3006 may be reversed. Moreover, it will be appreciated that the complementary mating surfaces of the universal stem and the unlinked bearing component 3004 and linked bearing component 3006 can be formed with various geometries as long as the complementary mating surfaces of both the unlinked bearing component 3004 and the linked bearing component 3006 can selectively and alternatively locate onto the first retaining mechanism 3020 of the universal stem 3002.

Once the first and second retaining mechanisms 3020 and 3066 have been positioned against each other, translation of the linked bearing component 3006 in the medial/lateral direction can be inhibited by the interaction of the extension portion 3022 and the groove 3068. Likewise, rotation of the linked bearing component 3006 around the ulnar ring 3014 can be inhibited by the interaction of the first and second anti-rotation portions 3024 and 3070, respectively. The catch 3032 can assist in further inhibiting rotational movement of the linked bearing component 3006. Next, the fastener 3008 can be advanced through the passage 3080 in the linked bearing component 3006 and threadably advanced into the threaded bore 3030 of the universal stem 3002 to further secure the linked bearing component 3006 to the universal stem 3002.

Figure 19:
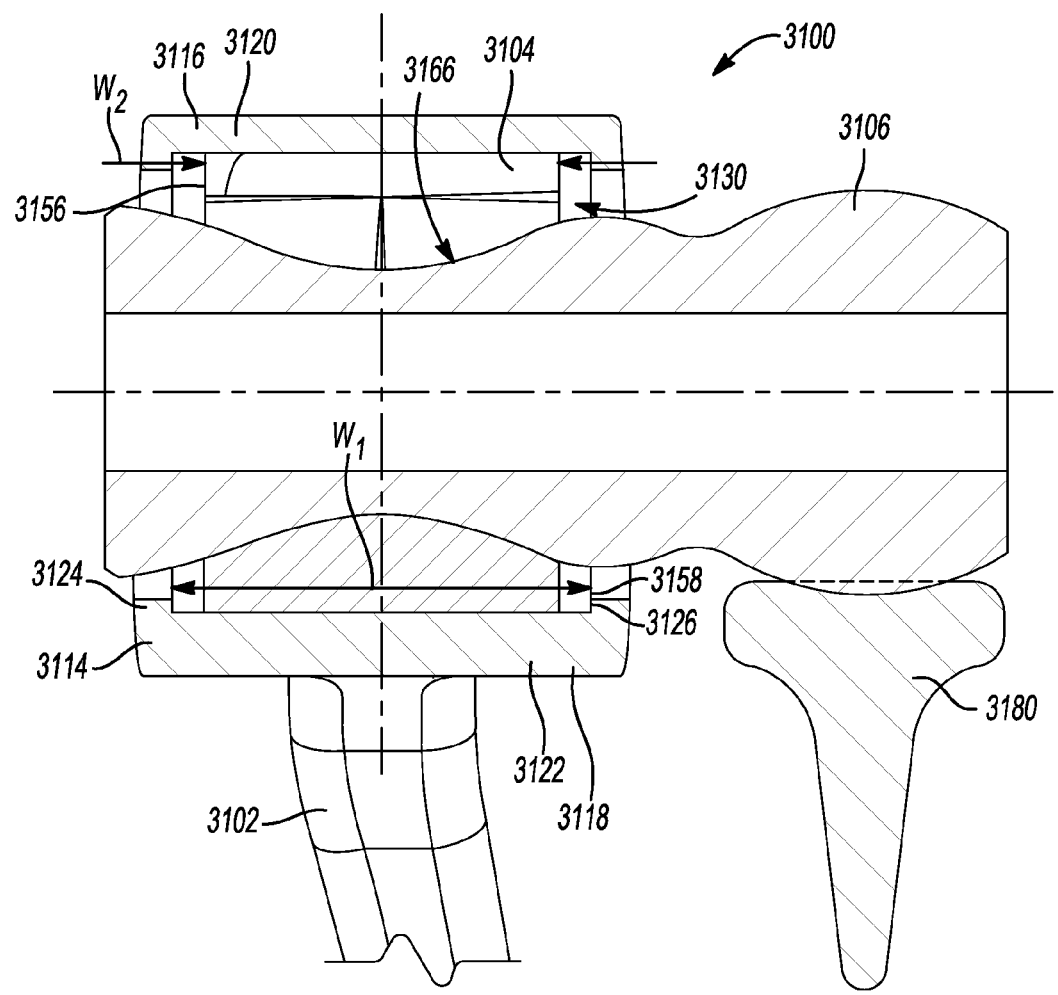
FIG. 19 is a cross-sectional view of the modular ulnar prosthesis of FIG. 13 and shown with an exemplary humeral component and radial component.

With reference now to FIGS. 12-18, a modular unlinked ulnar stem assembly 3100 constructed in accordance to one example of the present teachings will be described. In general, the modular unlinked ulnar stem assembly 3100 can include a stem structure 3102 and a mobile ulnar bearing 3104. As will become appreciated from the following discussion, the mobile ulnar bearing 3104 can be configured to slidably communicate along a surface of the stem structure 3102 in a medial/lateral direction. In addition, the mobile ulnar bearing 3104 can be configured to include dedicated surface areas that can be adapted to articulate against a surface of a distal unlinked humeral component 3106 (FIG. 19). The mobile ulnar bearing 3104 therefore can be configured to provide two articulations. A first articulation provided during medial/lateral translation of the mobile ulnar bearing 3104 along an opposing surface of the stem structure 3102 and a second articulation with the distal unlinked humeral component 3106. Again, as with the other embodiments disclosed herein, the mobile ulnar bearing 3104 can be modular, such that a series of mobile ulnar bearings 3104 can be provided that are each selectively configured for slidable movement along the stem structure 3102 according to a specific patient's needs. The modular unlinked ulnar stem assembly 3100 can be favorable in some circumstances as it has the potential to remove less native bone than other elbow prostheses, such as a semi-constrained total elbow, for example.

Figure 12:
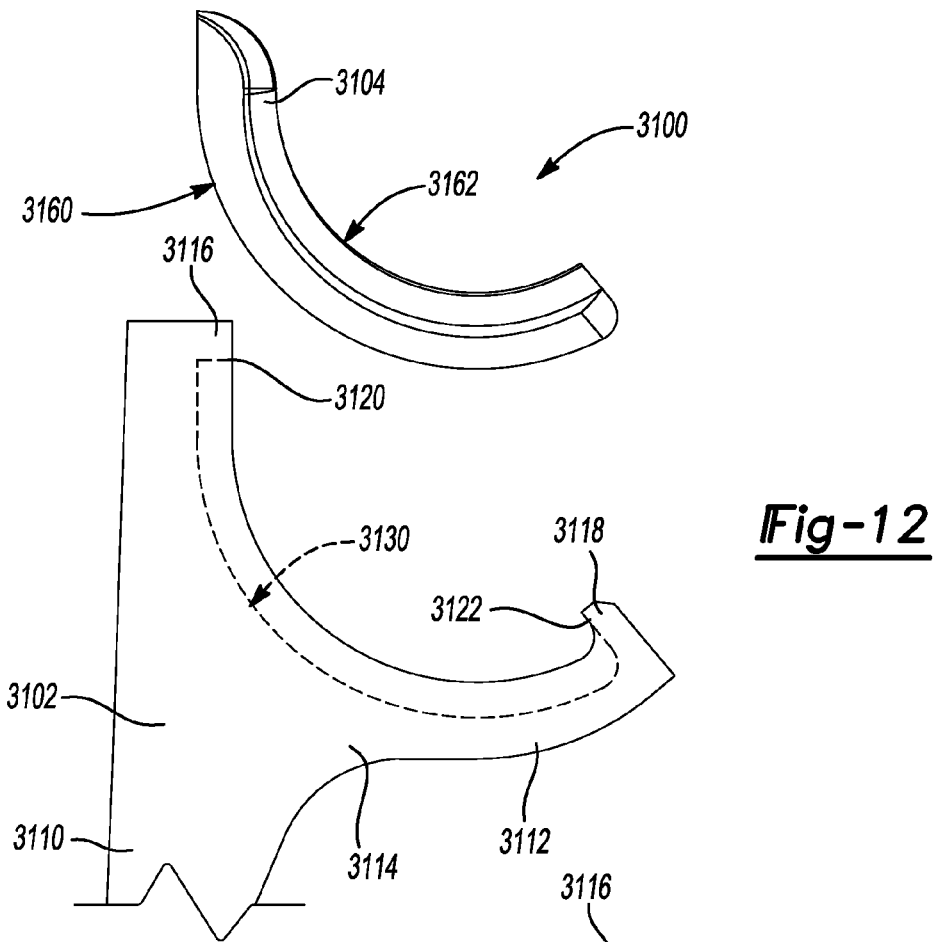
FIG. 12 is an exploded medial side view of a modular ulnar prosthesis that incorporates a mobile bearing.
Figure 13:
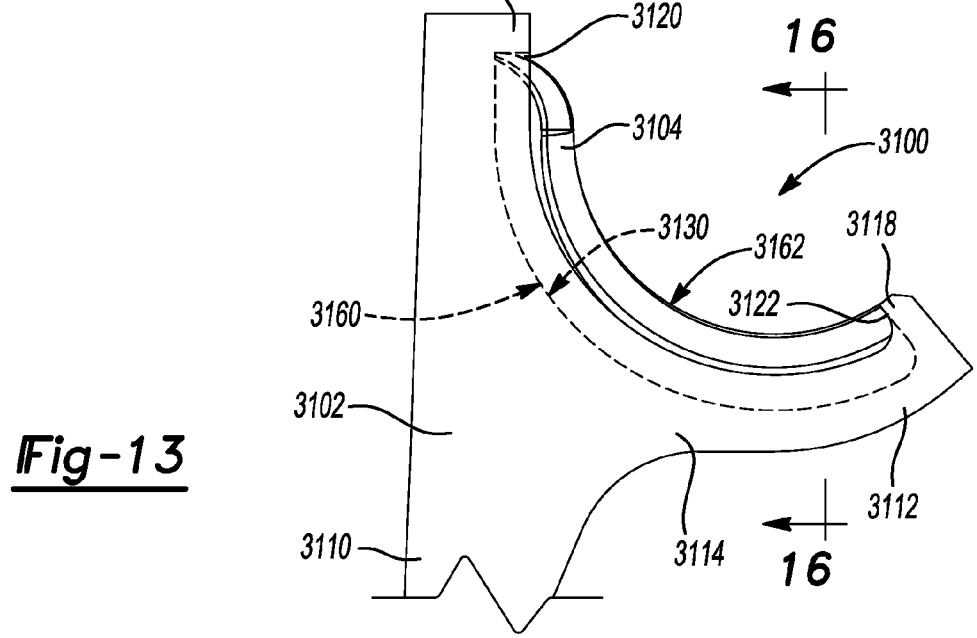
FIG. 13 is a medial side view of the modular ulnar prosthesis shown with the mobile bearing in an engaged position with the ulnar stem component.

With specific reference now FIGS. 12, 13 and 16 exemplary features of the stem structure 3102 will be described. The stem structure 3102 can generally include a stem portion 3110 and a C-shaped body portion 3112. In this regard, the body portion 3112 can generally include an ulnar ring 3114 that is in the form of a partial or semi-circular cylinder. The body portion 3112 can generally extend between a first end 3116 and a second end 3118. The body portion 3112 can further comprise a first wall 3120 arranged at the first end 3116 and a second wall 3122 arranged at the second end 3118.

The body portion 3112 can further comprise a medial wall 3124 and a lateral wall 3126 (FIG. 16). The first wall 3120, second wall 3122, medial wall 3124 and lateral wall 3126 can cooperate to provide a boundary that confines the mobile ulnar bearing 3104 as will be described more fully herein. A width W1 can be defined between the medial wall 3124 and the lateral wall 3126. The body portion 3112 can further provide an ulnar ring articulation surface 3130 that the mobile ulnar bearing 3104 slidably communicates therealong. As with the other examples provided herein, the stem structure 3102 can be formed of a biocompatible material, such as cobalt or titanium. The ulnar ring articulation surface 3130 of the stem structure 3102 can be highly polished to facilitate smooth translation of the mobile ulnar bearing 3104 thereal-ong.

Figure 14:
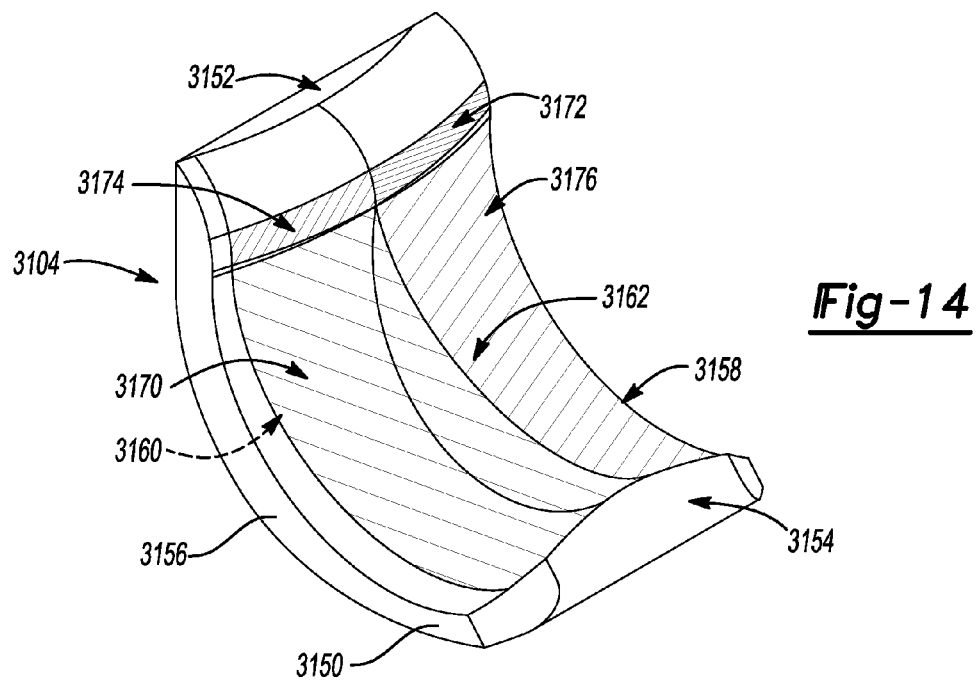
FIG. 14 is a perspective view of the mobile bearing of FIG. 12.
Figure 15:
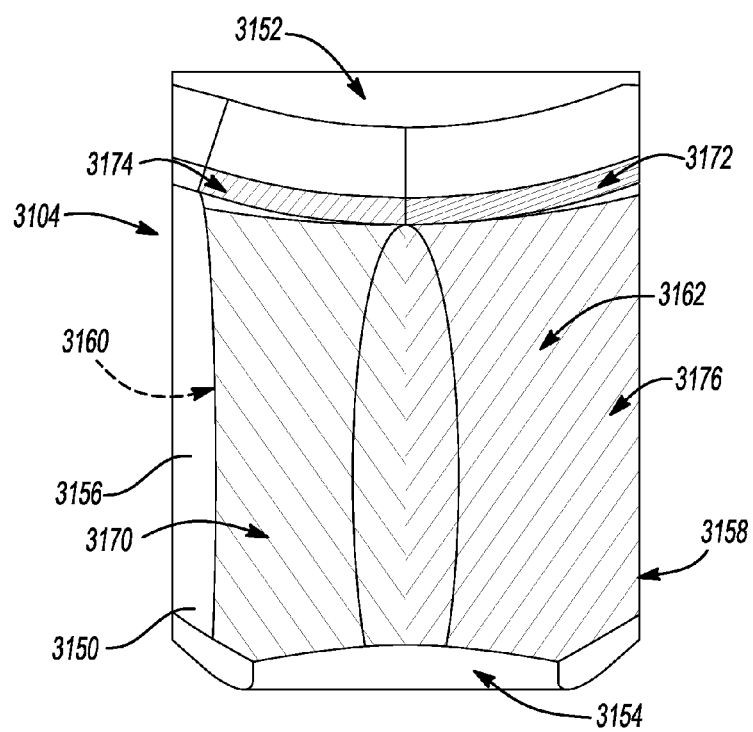
FIG. 15 is an anterior view of the mobile bearing of FIG. 14.

With general reference now to FIGS. 12-21 and specific reference to FIGS. 14 and 15, the mobile ulnar bearing 3104 will be described in greater detail. In general, the mobile ulnar bearing 3104 can include a body 3150 that generally takes the shape of a partial or semi-circular cylinder complementary to the shape of the ulnar ring 3114. The body 3150 can extend between a first end 3152 and a second end 3154. The body 3150 can further include a medial side surface 3156 and a lateral side surface 3158. The body 3150 can include an ulnar opposing articulating surface 3160 that slidably communicates along the ulnar ring articulating surface 3130 (FIG. 12) and a humeral opposing articulating surface 3162 that articulates with a humeral articulating surface 3166 of the distal unlinked humeral component 3106 (FIG. 19). The ulnar opposing articulating surface 3160 can be linear or spherical along a cross-section taken through a medial/lateral plane of the mobile ulnar bearing 3104. Likewise, the ulnar ring articulation surface 3130 can have a similar cross-sectional profile that matches the ulnar opposing articulating surface 3160.

The humeral opposing articulating surface 3162 can be collectively formed by a first articulating surface 3170, a second articulating surface 3172, a third articulating surface 3174 and a fourth articulating surface 3176. In the example shown, the first and second articulating surfaces 3170 and 3172 are arranged generally diagonally relative to each other while the third and fourth articulating surfaces 3174 and 3176, respectively are also arranged generally diagonally relative to each other. In this regard, the first, second, third and fourth articulating surfaces 3170, 3172, 3174 and 3176 can provide four quadrants that can be configured to selectively articulate along the humeral articulating surface 3166 according to a given varus or valgus movement. The configuration of the first, second, third and fourth articulating surfaces 3170, 3172, 3174 and 3176 can be particularly advantageous as they can selectively provide a relatively larger surface area contact with the humeral articulating surface 3166 of the distal unlinked humeral component 3106 as compared to a general line-to-line contact that may be achieved from other conventional mobile ulnar bearing configurations as will be described in detail herein.

With reference now to FIGS. 16-18, movement of the mobile ulnar bearing 3104 relative to the ulnar ring 3114 will be described. As identified above, the mobile ulnar bearing 3104 can be configured to slidably translate along the ulnar ring articulating surface 3130 in a medial/lateral direction. In this regard, the mobile ulnar bearing 3104 can define a width W2 between the medial side surface 3156 and the lateral side surface 3158. The width W2 can be less than the width W1 provided between opposing medial and lateral walls 3124 and 3126 of the ulnar ring 3114, such that the mobile ulnar bearing 3104 can slidably communicate along the ulnar ring articulating surface 3130 between the medial wall 3124 and the lateral wall 3126 of the ulnar ring 3114. As shown in FIG. 17, the mobile ulnar bearing 3104 can translate to a medial-most position where the medial side surface 3156 of the mobile ulnar bearing 3104 is in contact with the medial wall 3124 of the ulnar ring 3114. As can be appreciated, further translation of the mobile ulnar bearing 3104 in the medial direction is precluded by contact with the medial wall 3124. Similarly, the mobile ulnar bearing 3104 is shown in a lateral-most position in FIG. 18 where the lateral side surface 3158 is moved into contact with the lateral wall 3126 of the ulnar ring 3114. Again, further translation of the mobile ulnar bearing 3104 in the lateral direction is precluded by contact with the lateral wall 3126.

Figure 20:
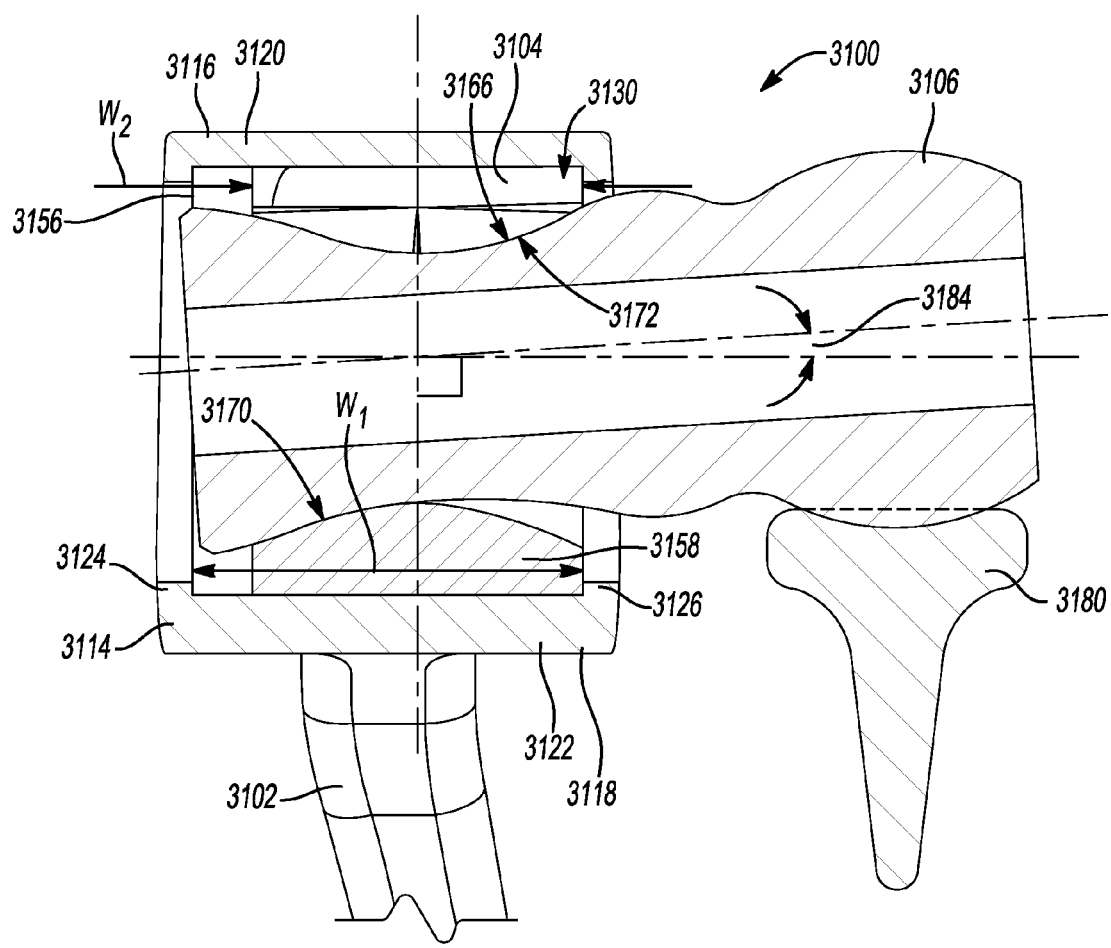
FIG. 20 is a cross-sectional view of the assembly of FIG. 19 and shown with the arm rotated into a varus position.
Figure 21:
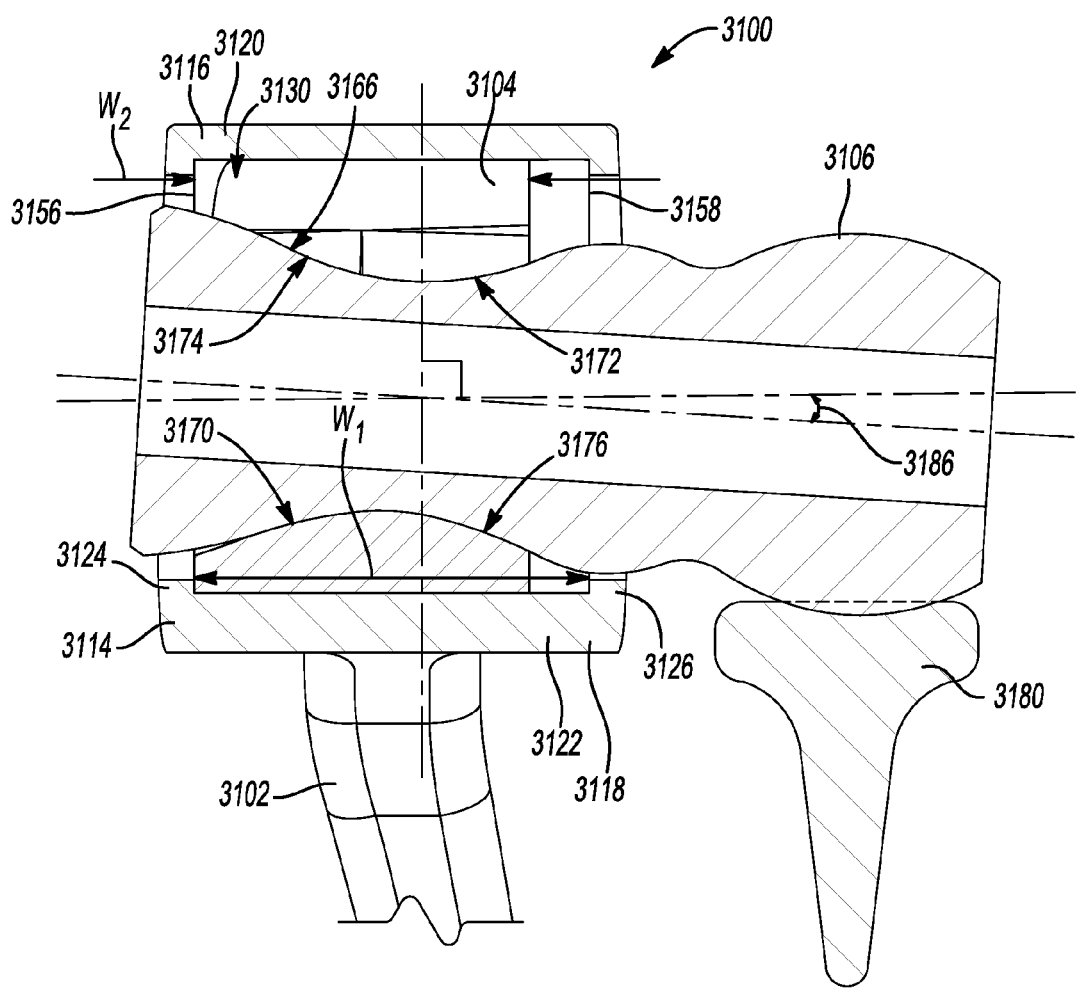
FIG. 21 is a cross-sectional view of the assembly of FIG. 19 and shown with the arm rotated into a valgus position.

With reference now to FIGS. 14 and 19-21, articulation of the mobile ulnar bearing 3104 with the distal unlinked humeral component 3106 will be further described. By way of example, the modular unlinked ulnar stem assembly 3100 is shown with the distal unlinked humeral component 3106 in a neutral position in FIG. 19. An exemplary radial component 3180 can be implanted if desired. In FIG. 20, the distal unlinked humeral component 3106 is shown during varus arm movement. In the exemplary configuration, the varus arm position can have an angle 3184 of about 3.5 degrees. In FIG. 21, the distal unlinked humeral component 3106 is shown in a valgus arm position. More specifically, the distal unlinked humeral component 3106 is shown rotated in angle 3186 of about 3.5 degrees. When the arm is in the varus position shown in FIG. 20, the humeral articulating surface 3166 of the distal unlinked humeral component 3106 can engage the first and second articulation surfaces 3170 and 3172 of the mobile ulnar bearing 3104. The surface profile of the first and second articulation surfaces 3170 and 3172 can provide a diagonally opposed surface contact with the humeral articulating surface 3166. Explained further, the cross-hatched surface areas 3170 and 3172 can both be contacting the humeral articulating surface 3166 thereby providing a supportive interface between the mobile ulnar bearing 3104 and the distal unlinked humeral component 3106 in the varus position. Such a configuration can provide a more stable surface-to-surface contact versus a line-to-line contact. Similarly, when the distal unlinked humeral component 3106 is moved to the corresponding valgus arm position shown in FIG. 21, the third and fourth articulation surfaces 3174 and 3176 of the mobile ulnar bearing 3104 can communicate with the humeral articulation surface 3166 of the distal unlinked humeral component 3106. Again, the surface profile of the third and fourth articulation surfaces 3174 and 3176 provided by the mobile ulnar bearing 3104 can provide a surface contact with the humeral articulation surface 3166 that can improve stability. Explained further, the cross-hatched surface areas 3174 and 3176 can both be contacting the humeral articulating surface 3166 thereby providing a supportive interface between the mobile ulnar bearing 3104 and the distal unlinked humeral component 3106 in the valgus position.

While the description in the specification and illustrated in the drawings are directed to various embodiments, it will be understood that various changes may be made and equivalents may be substituted for elements thereof without departing from the scope of the teachings and the appended claims. In addition, many modifications may be made to adapt a particular situation or material to the teachings without departing from the scope thereof. Therefore, it is intended that the teachings and claims are not to be limited to any particular embodiment illustrated in the drawings and described in the specification, but that the teachings and claims can include any embodiments falling within the foregoing description and the appended claims.

What is claimed:

1. An elbow prosthesis comprising:
    a stem structure operable to be positioned in a bone of a joint, the stem structure including:
        a stem portion operable to be positioned in the bone; and
        a C-shaped body portion having a first retaining mechanism formed thereon;
    an articulating component having a second retaining mechanism formed thereon and a bearing portion opposite the second retaining mechanism, the bearing portion having a first end defining a passage adapted to receive a fastener therethrough, and a second end; and
    wherein one of the first and second retaining mechanisms comprises an extension portion and a first anti-rotation portion and the other of the first and second retaining mechanisms comprises a receiving portion and a second anti-rotation portion, wherein the articulating component is advanced from an insertion position to an assembled position such that the first and second retaining mechanisms cooperatively mate to inhibit translation and rotation of the articulating component relative to the C-shaped body portion of the stem structure,
    wherein the C-shaped body portion includes a catch extending from an end of the body portion, the catch being angled toward and adjacent to the second end of the bearing portion in the assembled position;
    wherein the extension portion comprises a radially arcuate rail and the receiving portion comprises a groove that receives the rail in the assembled position; and
    wherein the first anti-rotation portion comprises a first undulating shape including a first series of peaks and valleys and the second anti-rotation portion comprises a second undulating shape including a second series of peaks and valleys that cooperatively mates with the first undulating shape in the assembled position.

2. The elbow prosthesis of claim 1 wherein the articulating component comprises the groove, and the second end of the bearing portion includes a relief.

3. The elbow prosthesis of claim 1 wherein the fastener threadably couples the articulating component to the stem structure.

* * * * *